US012706209B2

(12) United States Patent
Van Der Zalm et al.

(10) Patent No.: US 12,706,209 B2
(45) Date of Patent: Aug. 11, 2026

(54) IMPLANTABLE ELECTRICAL DEVICE COMPRISING A SUBSTRATE, ENCAPSULATION LAYER AND ADHESION LAYER

(71) Applicant: SALVIA BIOELECTRONICS B.V., Eindhoven (NL)

(72) Inventors: Maartje Van Der Zalm, Eindhoven (NL); Stijn Willem Boere, Eindhoven (NL)

(73) Assignee: Salvia BioElectronics B.V., Eindhoven (NL)

(*) Notice: Subject to any disclaimer, the term of this patent is extended or adjusted under 35 U.S.C. 154(b) by 793 days.

(21) Appl. No.: 17/913,400

(22) PCT Filed: Apr. 1, 2021

(86) PCT No.: PCT/EP2021/058751
§ 371 (c)(1),
(2) Date: Sep. 21, 2022

(87) PCT Pub. No.: WO2021/198484
PCT Pub. Date: Oct. 7, 2021

(65) Prior Publication Data

US 2023/0113727 A1 Apr. 13, 2023

(30) Foreign Application Priority Data

Apr. 3, 2020 (NL) ...................................... 2025268
Dec. 4, 2020 (WO) .................. PCT/IB2020/061474

(51) Int. Cl.
*G16H 40/67* (2018.01)
*A61B 5/24* (2021.01)

(52) U.S. Cl.
CPC ............... *G16H 40/67* (2018.01); *A61B 5/24* (2021.01)

(58) Field of Classification Search
CPC ................................. G16H 40/67; A61B 5/24
See application file for complete search history.

(56) References Cited

U.S. PATENT DOCUMENTS 11,129,986 B2 * 9/2021 Schobben ............ A61N 1/0551
11,318,319 B2 * 5/2022 Schobben .......... A61N 1/36007
(Continued)

FOREIGN PATENT DOCUMENTS

CN 104797291 A 7/2015
CN 107148294 A 3/2016
(Continued)

OTHER PUBLICATIONS

Li et al. "Ultra-Long-Term Reliable Encapsulation Using an Atomic Layer Deposited HfO2/AI2O3/HfO2 Triple-Interlayer for Biomedical Implants" (Year: 2019).*
(Continued)

*Primary Examiner* — Shirley X Jian
(74) *Attorney, Agent, or Firm* — Fresh IP PLC; Clifford D. Hyra; Aubrey Y. Chen

(57) ABSTRACT

Implantable devices require protection to protect a human or animal body from implant contamination and to protect implant electrical connections and electronics from corrosion. Although PDMS can be substantially biocompatible, it still has a relatively high permeability to moisture which can lead to degradation of the implant electronics.
An implantable electric device is provided comprising: a flexible substrate having one or more electrical conductors and a first surface comprising a Liquid-Crystal Polymer (LCP); a first biocompatible encapsulation layer; a first adhesion layer disposed between the first surface and the first encapsulation layer; wherein: the first adhesion layer comprises a ceramic material; the first encapsulation layer comprises a silicone rubber such as a PDMS, and the first adhesion layer and the first encapsulation layer are config-
(Continued)

ured and arranged to conform to the first surface and to resist the ingress of fluids into at least a portion of the first surface. By providing a bilayer having an encapsulant comprising a silicone rubber and a conformal adhesion layer comprising ceramic materials, the adhesion layer appears to show significantly higher stability in ionic media, thereby providing relatively longer protection in case of any delamination or water permeation through the encapsulant.

23 Claims, 9 Drawing Sheets

(56) References Cited

U.S. PATENT DOCUMENTS

2002/0198582 A1* 12/2002 Edell ........................ A61N 1/05 607/116
2006/0173497 A1 8/2006 Mech et al.
2007/0128420 A1 6/2007 Maghribi
2010/0148345 A1* 6/2010 Eckhardt ............. H01L 23/4985 438/653
2011/0015686 A1* 1/2011 Kara ...................... A61N 1/375 427/2.24
2012/0323288 A1 12/2012 Anderson et al.
2013/0296988 A1 11/2013 Weber et al.
2013/0303873 A1 11/2013 Voros et al.
2014/0031889 A1* 1/2014 Mashiach ................ H04B 5/22 29/601
2015/0142083 A1* 5/2015 Yomtov ................... A61N 1/05 607/61
2015/0157862 A1 6/2015 Greenberg et al.
2016/0067477 A1 3/2016 Dubuclet
2017/0080216 A1 3/2017 Pham
2017/0304630 A1 10/2017 Plachta et al.
2021/0170176 A1* 6/2021 Martens ............. A61N 1/36075

FOREIGN PATENT DOCUMENTS

JP 2007167636 7/2007
JP 2008528237 7/2008
JP 2012010978 1/2012
JP 2017525509 5/2017
JP 2018149361 9/2018
WO 2015107515 A1 7/2015
WO 2016033369 A1 3/2016
WO 2019124566 A1 6/2019

OTHER PUBLICATIONS

Biosynethetic Polymers for Medical application, Chapter 2: Non-degradable synthetic polymers for medical devices and implants (Year: 2016).*

Office Action dated Dec. 27, 2024, issued in JP Patent Application No. JP2022-532873, 6 pages.

Office Action dated Mar. 5, 2024, issued in JP Patent Application No. JP2022-532873; 5 pages.

Search Report for International Patent Application PCT/EP2021/058751, mailed on Jun. 22, 2021.

Vajari D Ashouri et al: "Hybrid multimodal Deep Brain probe (DBS array) for advanced brain research," 2015 7th International IEEE/EMBS Conference on Neural Engineering (NER), IEEE, Apr. 22, 2015, pp. 280-283.

First Examination report dated Sep. 18, 2025, issued in IN Patent Application No. 202227029826; 6 pages.

* cited by examiner

IMPLANTABLE ELECTRICAL DEVICE COMPRISING A SUBSTRATE, ENCAPSULATION LAYER AND ADHESION LAYER

FIELD

The present disclosure relates to an implantable electrical device comprising a substrate, one or more encapsulation layers and one or more adhesion layers. In particular, it relates to an implantable medical device comprising one or more electrodes.

BACKGROUND

Implantable active devices require a protection method to protect the implant electronics from bodily fluids present in human or animal bodies. Bodily fluids typically contain ions that may cause electrochemical reactions, like corrosion, in the presence of an electric current. Encapsulation is thus a critical component for the design of a medical device—it acts as a barrier between these ionic fluids and critical electronic/electric interfaces to reduce and/or prevent degradation of the implant electronics.

Polyimides are popular for use as a substrate material for the microfabrication of electronics, and attempts have been made to encapsulate polyimides with silicone rubber encapsulants, such as polydimethylsiloxane rubber (PDMS). As described in "Irreversible bonding of polyimide and polydimethylsiloxane (PDMS) based on a thiol-epoxy click reaction", Hoang, Chung and Elias, Journal of Micromechanics and Microengineering, 10.1088/0960-1317/26/10/105019, bonding these two flexible materials remains a crucial challenge—the resistance to fluid ingress may be reduced by the encapsulant delaminating to some degree from the substrate. The degree of bonding was increased by functionalizing the surfaces of the PDMS and polyimide substrates with mercaptosilanes and epoxysilanes, respectively, for the formation of a thiolepoxy bond in the click reaction. It was also increased by functionalizing one or both surfaces with mercaptosilane and introducing an epoxy adhesive layer between the two surfaces.

US patent application US 2011/0015686 A1 describes a method of adhering a protective layer applied to a substrate region of an implantable medical device (IMD) to form a covered Substrate region. The method includes obtaining the IMD, depositing an intermediate layer on a portion of the substrate region of the IMD such that the intermediate layer binds to the portion of the Substrate region to create a modified substrate region, and depositing the protective layer after depositing the intermediate layer onto the intermediate layer and adhering the protective layer to the intermediate layer. In an embodiment of the present invention, this method enhances the sealing characteristics of the protective layer by, for example, reducing the likelihood of delamination of the protective layer from the IMD relative to IMDs prepared by certain other methods.

"Hybrid multimodal Deep Brain probe (DBS array) for advanced brain research", VAJARID ASHOURI ET AL, 2015 7TH INTERNATIONAL IEEE/EMBS CONFERENCE ON NEURAL ENGINEERING (NER), IEEE, 22 Apr. 2015, DOI: 10.1109/NER.2015.7146614 describes a hybrid multimodal deep brain probe made out of a thin-film polyimide electrode and flexible silicone rubber substrate. The engineered combination of two technologies resulted in a device as flexible as commercial DBS probes, but including the benefits from thin-film technology such as higher contact density, high resolution in fabrication and capability of applying various coatings for specific applications US patent application US 2007/0128420 A1 describes a hybrid composite for medical devices that interface with biological tissues. The hybrid composite comprises at least one first layer of conformable polymeric material, a second layer of insulating polymeric material, and one or more active components and/or one or more passive components, wherein the one or more active components and/or the one or more passive components are partially or completely embedded in the first layer of conformable polymeric material or the second layer of insulating polymeric material. Preferably, the conformable polymeric material is an elastomer, a hydrogel or a biodissolvable polymer and the insulating polymeric material is parylene or silicon carbide. A method of forming the inventive hybrid composite is also provided.

Although PDMS can be substantially biocompatible, causing minimal tissue reaction while having a relative long period of biostability, it still has a relatively high permeability to moisture which can lead to degradation of the implant electronics. Many other encapsulants with a lower degree of moisture permeability may have a lower degree of biocompatibility. Recently. LCP's (Liquid Crystal Polymers) have been considered for use as a substrate for electronics, and there is also a need for improved bonding techniques between LCP and encapsulants.

It is an object of the invention to provide improved bonding to improve resistance to fluid ingress in implantable devices comprising flexible substrates.

SUMMARY

According to a first aspect of the present disclosure, there is provided an implantable electrical device comprising: a flexible substrate having a first surface and one or more electrical conductors; a first biocompatible encapsulation layer; a first adhesion layer, disposed between the first surface and the first encapsulation layer; wherein: the first surface comprises a Liquid-Crystal Polymer (LCP), the first adhesion layer is configured and arranged to conform to the first surface and comprises a ceramic material; the first encapsulation layer comprises a silicone rubber (such as a polydimethylsiloxane (PDMS) rubber), and the first adhesion layer and the first encapsulation layer are configured and arranged to resist the ingress of fluids from a human or animal body into at least a portion of the first surface.

By providing a bilayer having an encapsulant comprising a silicone rubber and a conformal adhesion layer comprising ceramic materials, the adhesion layer appears to show significantly higher stability in ionic media, thereby providing relatively longer protection in case of any delamination or water permeation through the encapsulant. A silicone rubber, such as a PDMS, may further contribute to longer-lasting adhesion and defect reduction due to flowing in-between any defects and crevices in the adhesion layer—in particular, a silicone rubber, such as a PDMS with a relatively low viscosity may provide an even higher degree of defect reduction.

According to a further aspect of the current disclosure, there is provided an implantable electrical device, wherein the substrate further comprises a second surface, the electrical device further comprising: a second biocompatible encapsulation layer; and a second adhesion layer, disposed between the second surface and the second encapsulation layer, wherein: the second surface comprises a Liquid-Crystal Polymer (LCP); the second adhesion layer is configured and arranged to conform to the second surface 420 and comprises a ceramic material; the second encapsulation layer comprises a silicone rubber (such as a polydimethylsiloxane (PDMS) rubber), and the second adhesion layer and the second encapsulation layer are configured and arranged to resist the ingress of fluids from a human or animal body into at least a portion of the second surface.

One or more regions of a substrate surface may be protected by an encapsulant/adhesion layer. Each encapsulant/adhesion layer may be optimized separately or together to a predetermined degree.

According to a further aspect of the current disclosure, there is provided an implantable electrical device wherein the first surface and/or second surface comprise a substance selected from the group comprising: a polyimide, Parylene-C, SU-8, a polyurethane, or any combination thereof.

The encapsulant/adhesion layer may be optimized to protect a surface of many types of substrates. If the substrate is configured and arranged to be substantially flexible, the substrate may have a high degree of conformability. The high degree of adhesion of the encapsulant/adhesion layer allows the flexible encapsulant layer to provide a high degree of ingress protection for one or more surfaces of a flexible substrate.

According to another aspect of the current disclosure, there is provided an implantable electrical device, wherein the ceramic material is selected from the group comprising: $HfO_2$, $Al_2O_3$, $Ta_2O_3$, SiC, $Si_3N_4$. $TiO_2$, and any combination thereof.

These ceramic materials may be advantageously used as in an adhesion layer for a silicone rubber encapsulant layer, such as a PDMS encapsulant layer.

An adhesion layer may comprise more than one ceramic material. Multilayer stacks may be used comprising adjacent layers of similar and/or different ceramic materials. For example:

- the first and/or second adhesion layer may comprise at least one layer comprising $HfO_2$, adjacent to at least one further layer comprising $Al_2O_3$ Additionally or alternatively:
- the first and/or second adhesion layer may comprise at least one layer comprising $Ta_2O_3$, adjacent to at least one further layer comprising $Al_2O_3$.

According to yet another aspect of the current disclosure, there is provided an implantable medical device, comprising an implantable electrical device as described herein.

The implantable medical device is typically configured and arranged such that materials in direct contact with tissue are substantially biocompatible.

According to a further aspect of the current disclosure, there is provided a process for applying an encapsulation layer to a surface of a flexible substrate, the process comprising: providing a substrate having one or more electrical conductors and a first surface comprising a Liquid-Crystal Polymer (LCP); applying a first conformal adhesion layer, comprising a ceramic material, to at least a portion of the first surface; applying a first biocompatible encapsulation layer, comprising a silicone rubber (such as a polydimethylsiloxane (PDMS) rubber) to at least a portion of the first adhesion layer, wherein the first adhesion layer and the first encapsulation layer are configured and arranged to resist the ingress of fluids from a human or animal body into at least a portion of the first surface.

According to a still further aspect of the current disclosure, wherein the substrate has a second surface comprising a Liquid-Crystal Polymer (LCP), there is provided a process for further applying a second conformal adhesion layer, comprising a ceramic material, to at least a portion of the second surface; applying a second biocompatible encapsulation layer, comprising a silicone rubber (such as a polydimethylsiloxane (PDMS) rubber), to at least a portion of the second adhesion layer; wherein the second adhesion layer and the second encapsulation layer are configured and arranged to resist the ingress of fluids from a human or animal body into at least a portion of the second surface.

According to a yet further aspect of the current disclosure, there is provided a process wherein first adhesion layer and/or second adhesion layer is/are applied using an ALD process.

According to another aspect of the current disclosure, there is provided a process wherein the process further comprises: cleaning at least a portion of the first adhesion layer and/or second adhesion layer before applying the first and/or second encapsulation layer;

For example, the cleaning step may comprise: applying an alcohol, in particular ethanol, to at least a portion of the first adhesion layer and/or second adhesion layer; exposing at least a portion of the first adhesion layer and/or second adhesion layer to a plasma comprising $O_3$ (Ozone); exposing at least a portion of the first adhesion layer and/or second adhesion layer to a plasma comprising $O_2$; exposing at least a portion of the first adhesion layer and/or second adhesion layer to a silane; or any combination thereof.

According to a still further aspect of the current disclosure, there is provided a process wherein the first and/or second biocompatible encapsulation has an average viscosity in the range 4000 to 7000 mPas for a significant time period during the application to the first and/or second adhesion layers respectively.

Alternatively, the first and/or second biocompatible encapsulation has an average viscosity in the range 50000 to 100000 mPas for a significant time period during the application to the first and/or second adhesion layers respectively.

Advantageously, the first and/or second biocompatible encapsulation may be applied using a vacuum centrifugal casting.

BRIEF DESCRIPTION OF THE DRAWINGS

Features and advantages of some embodiments of the present invention, and the manner in which the same are accomplished, will become more readily apparent upon consideration of the following detailed description of the invention taken in conjunction with the accompanying drawings, which illustrate preferred and exemplary embodiments, and which are not necessarily drawn to scale, wherein.

DETAILED DESCRIPTION

In the following detailed description, numerous non-limiting specific details are given to assist in understanding this disclosure. It will be obvious to a person skilled in the art that the software methods may be implemented on any type of suitable controllers, memory elements, and/or computer processors.

Figure 1A:
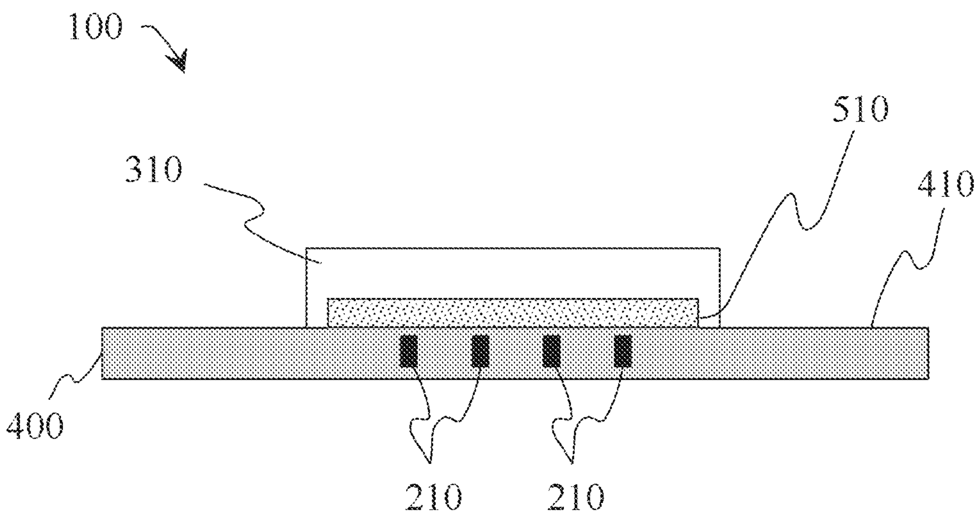
FIG. 1A, FIG. 1B and FIG. 1C depict cross-sections through improved implantable electrical devices.

FIG. 1A depicts a cross-section through an improved implantable electrical or electronic device 100. It comprises:

a substrate 400 having a first surface 410 and one or more electrical conductors 210.

Optionally, the substrate 400 may be substantially biocompatible—however, the use of one or more encapsulation layers 310 may allow substrates 400 and electrical conductors 210 which are not biocompatible, partially biocompatible, or significantly biocompatible, to be used.

In general, the degree of biocompatibility of a material or layer may be determined by measuring the degree of tissue reaction and the length of period during which it is considered biostable. A low degree of tissue reaction and/or long period of biostability indicates a high degree of biocompatibility.

The substrate 400 is further configured and arranged to be substantially flexible—in other words, the substrate is pliant or flexible or compliant (or conformable) to a substantial degree. The degree of flexibility may be adapted using parameters, such as:

dimensioning of the device 100 elements, and/or inclusion of materials and substances with desired properties, and/or combinations of materials and substances used, and/or percentages of materials and substances used, and/or inclusion of recesses, openings, apertures, reinforcement.

Additionally or alternatively, the skilled person will realize that the degree of flexibility and/or conformability of one or more portions of the substrate 400 may be adapted using one or more of the suitable parameters described in this disclosure.

The one or more electrical conductors 210 are depicted very schematically—they may be conductors embedded in or deposited onto the substrate 400—for example, by having a single polymer layer and applying conductive material using suitable deposition techniques known from the semiconductor industry. The one or more conductors 210, such as a metal, may be formed as required—for example, in one or more conductive elements: wire, strand, foil, lamina, plate, and/or sheet. Optionally, the one or more conductors may be positioned between the outer surfaces of the substrate 400;

The device 100 further comprises:

a first biocompatible encapsulation layer 310 comprising a poly dimethylsiloxane (PDMS) rubber; and a first adhesion layer 510, In the context of this disclosure, a ceramic should be considered as an advanced ceramic and/or an industrial ceramic, providing a relatively high degree of thermal stability, wear-resistance and resistance to corrosion.

The most suitable ceramic materials are those with a high degree of adhesion to the encapsulant layer and/or substrate, and capable of being applied in a relatively uniform coating to provide a relatively low degree of permeability to moisture. A ceramic material in this context may be an inorganic, non-metallic or metallic, often crystalline oxide, nitride or carbide material. Some elements, such as carbon or silicon, are also considered ceramics. A non-metallic ceramic may comprise both non-metallic and metallic elements.

Optionally, the first adhesion layer 510 may be substantially biocompatible—however, the use of one or more encapsulation layers 310 may allow one or more adhesion layers 510 which are not biocompatible, partially biocompatible, or significantly biocompatible, to be used.

The first adhesion layer 510 and the first encapsulation layer 310 are configured and arranged to resist the ingress of fluids from a human or animal body into at least a portion of the first surface 410. The configuration and arrangement are further described below.

Figure 1B:
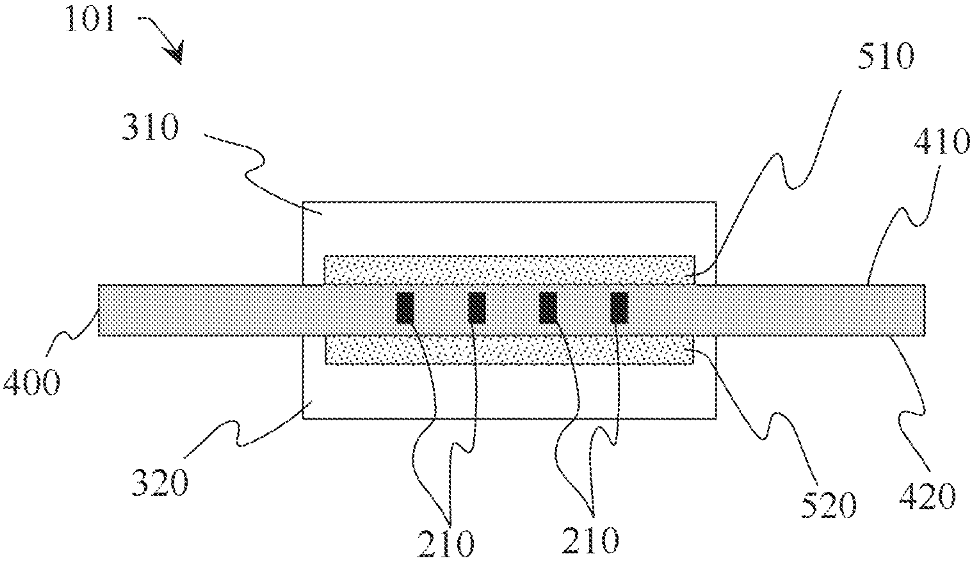
Figure 1C:
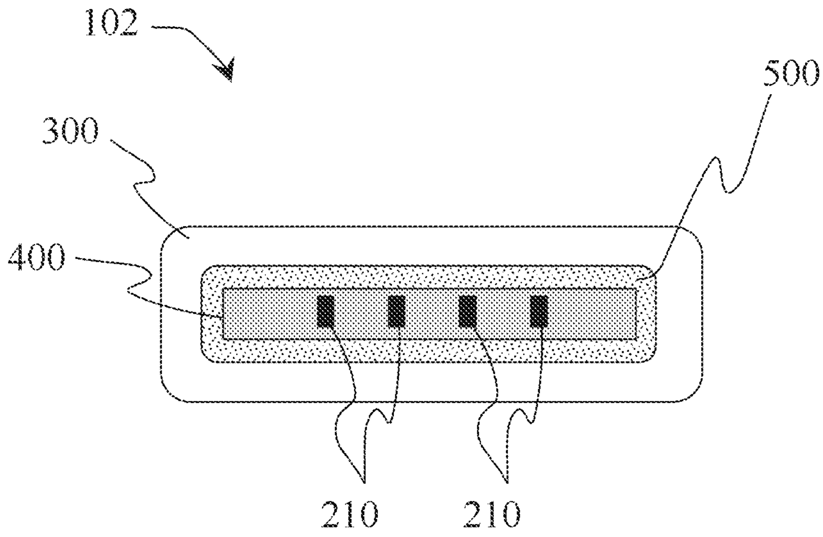
Figure 2A:
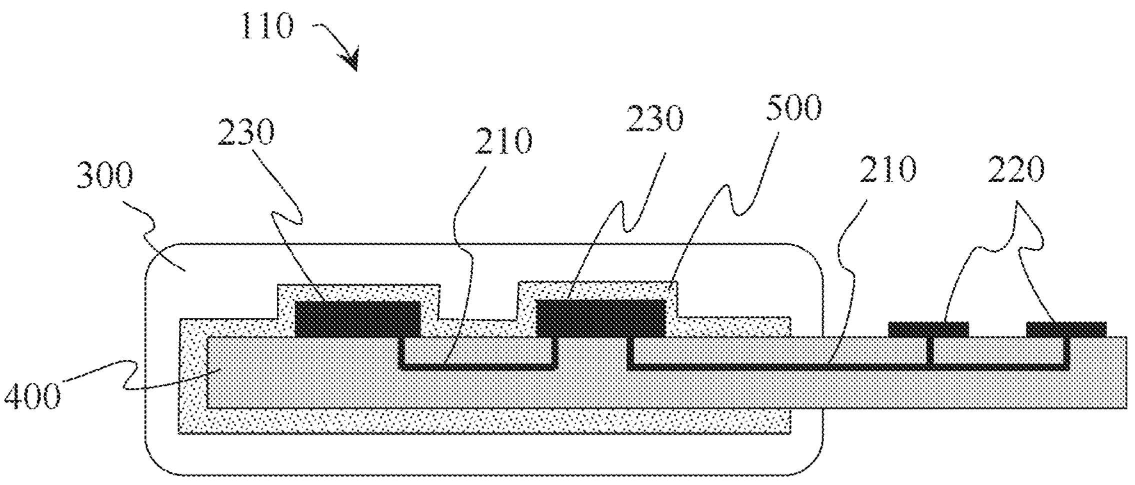
FIG. 2A and FIG. 2B depict cross-sections through improved implantable medical devices comprising an improved implantable electrical device, and one or more electrodes.

As depicted in FIG. 1A, the extent of the adhesion/encapsulation layer 510/310 in this cross-section may be less than the extent of the substrate 400. In general, the extent of the adhesion/encapsulation layer 510/310 may be larger than, equal to or less than the extent of the substrate 400. A "larger than" embodiment for the adhesion and encapsulation layers is depicted in FIG. 1C. Further "less than" embodiments for the adhesion and encapsulation layers are depicted in FIG. 1B and FIG. 2A.

In general, the portion of the first surface 410 being protected against ingress of fluids is equal to or less than the extent of the adhesion/encapsulation layer 510/310.

Figure 2B:
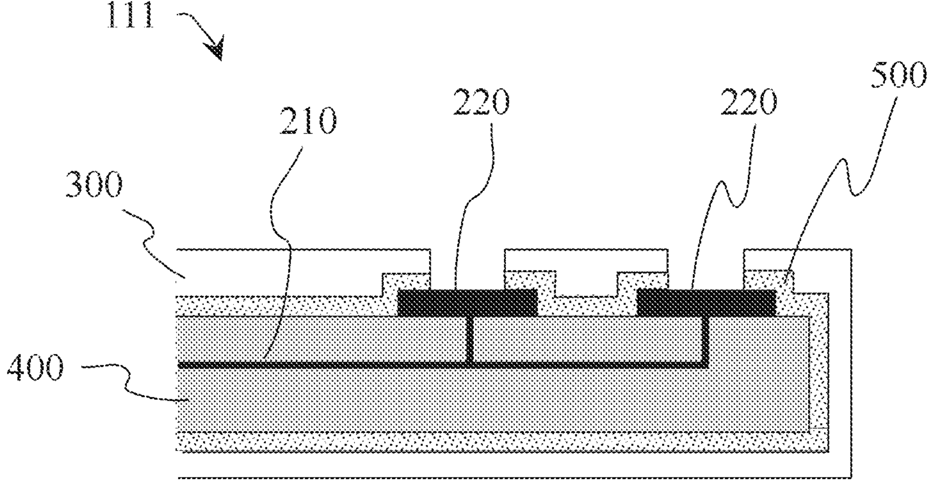

As depicted in FIG. 1A, the extent of the adhesion layer 510 in this cross-section may be less than the extent of the encapsulation layer 310—in some configurations, this may be advantageous as the edges of the adhesion layer 510 are at least partially encapsulated 310. In general, the extent of the adhesion layer 510 may be larger than, equal to or less than the extent of the encapsulation layer 310. Further "less than" embodiments are depicted in FIG. 1C and FIG. 2A. An "equal to" portion of a substrate is depicted in FIG. 2B.

In a preferred embodiment, the extent of the adhesion layer 510 is equal to or larger than the extent of the encapsulation layer 310—this may be advantageous in certain configurations as the surface area of encapsulant 310 in direct contact with the surface 410 of the substrate 400 is greatly reduced. In some cases, this surface area may be substantially zero, further reducing the possibility of fluid ingress. A"substantially zero" embodiment is depicted in FIG. 1C and a portion of a substrate depicted in FIG. 2B.

FIG. 1B depicts another implantable electrical or electronic device 101. It is the same as the implantable electrical device 100 depicted in FIG. 1A, except for further comprising:

a second surface 420;

a second biocompatible encapsulation layer 320, comprising a polydimethylsiloxane (PDMS) rubber; and a second adhesion layer 520, comprising a ceramic material, disposed between the second planar surface 420 and the second encapsulation layer 320. The second adhesion layer 520 is further configured and arranged to conform to the second surface 420—in other words, it is a conformal layer.

The second adhesion layer 520 and the second encapsulation layer 320 are configured and arranged to resist the ingress of fluids from a human or animal body into at least a portion of the second surface 420. The configuration and arrangement are further described below.

The second encapsulation layer 320 may be substantially identical, similar to a high degree or substantially different to the first encapsulation layer 310.

The second adhesion layer 520 may be substantially identical, similar to a high degree or substantially different to the first adhesion layer 510.

Although the first surface 410 and second surface 420 are depicted as opposite faces of a substrate in FIG. 1B, other combinations are possible, such as:

- applying the first adhesion/encapsulation layer 310/510 and the second adhesion/encapsulation layer 320/520 to different regions of the first surface 410;
- applying the first adhesion/encapsulation layer 310/510 and the second adhesion/encapsulation layer 320/520 to different regions of the second surface 420;
- the first surface 410 and second surface 420 being adjacent to each other,
- the first surface 410 and second surface 420 being opposite to each other;
- the first surface 410 and second surface 420 being at a predetermined angle to each other;
- the first surface 410 and second surface 420 being substantially perpendicular to each other.

FIG. 1C depicts a further implantable electrical or electronic device 102. It is the same as the implantable electrical device 100 depicted in FIG. 1A, except in this cross-section:

- the substrate 400 comprises four protected surfaces, each surface being protected by a further adhesion layer 500 and a further encapsulation layer 300;
- the extent of the further adhesion layer 500 is larger than the extent of substrate 400 for each protected surface;
- the extent of the further encapsulation layer 300 is larger than the extent of the substrate 400 for each protected surface; and
- the extent of the further adhesion layer 500 is less than the extent of the encapsulation layer 300 for each protected surface.

Functionally, it may also be considered that the further encapsulation layer 300 comprises the first 310 and second 320 encapsulation layers depicted in FIG. 1B.

Functionally, it may also be considered that the further adhesion layer 500 comprises the first 510 and second 520 adhesion layers depicted in FIG. 1B.

Functionally, it may also be considered that the substrate 400 depicted in FIG. 1C comprises the protected portions of the first 410 and second 420 surfaces depicted in FIG. 1B. However, the substrate 400 depicted in FIG. 1C, comprises two or more further protected surfaces, adjacent to such a protected first or second surface.

The further encapsulation layer 300 of FIG. 1C may be substantially identical, similar to a high degree or substantially different to the first encapsulation layer 310 depicted in FIG. 1A or 1B. The further encapsulation layer 300 of FIG. 1C may be substantially identical, similar to a high degree or substantially different to the second encapsulation layer 320 depicted in FIG. 1B.

The further adhesion layer 500 of FIG. 1C may be substantially identical, similar to a high degree or substantially different to the first adhesion layer 510 depicted in FIG. 1A or 1B. The further adhesion layer 500 of FIG. 1C may be substantially identical, similar to a high degree or substantially different to the second adhesion layer 520 depicted in FIG. 1B.

The further embodiment 102 may be advantageous because:

- the portion of the surfaces of the substrate 400 being protected against ingress of fluids is less than the extent of the further encapsulation layer 300;
- the edges of the further adhesion layer 500 are substantially encapsulated 300; and
- the surface area of encapsulant 300 in direct contact with a surface of the substrate 400 is close to or substantially zero.

Experiments were performed to establish the suitability of a specific adhesion layer 510, 520 to provide a high degree of bonding to a PDMS.

A. Sample Preparation

Figure 3:
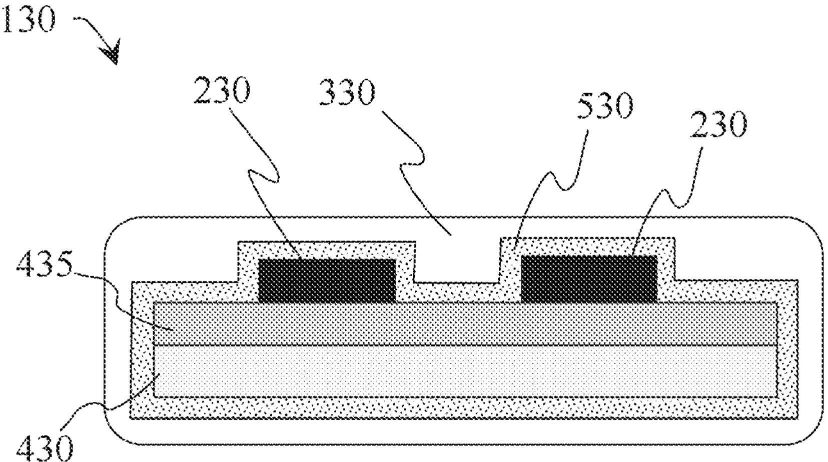
FIG. 3 depicts a cross-section through a test sample.

FIG. 3 depicts a cross-section through the test sample 130

1) IDC Using Pt Metallization

Interdigitated capacitors (IDC) 230 were used to evaluate encapsulation performance—approximately 600 nm of Pt (Platinum) was sputtered on top of a 1 μm (1 micron) thick plasma enhanced chemical vapor deposition (CVD) SiO2 layer 435 with an intermediate 10 nm titanium adhesion layer. More details on these IDC 230 are found in "Silicone rubber encapsulation for an endoscopically implantable gastrostimulator". Lonys, Vanhoestenberghe, Julemont, Godet, Delplancke, Mathys and Nonclercq, Med. Biol. Eng. Comput. 53 319-29, 2015. The SiO2 layer 435 was provided on a silicon substrate 430.

2) ALD Coating

Atomic layer deposition (ALD) is a coating process that may be used to create nm-thick conformal coatings. The ALD coating was applied using the PICOSUN® R-200 Advanced ALD reactor under reduced pressure (N2 atmosphere) of about 1 mbar (1 hPa).

The R-200 Advanced, from Picosun Oy, Finland, provides very high quality ALD film depositions. It is suggested by the manufacturer as suitable for depositions including: Al2O3, TiO2, SiO2, Ta2O5, HfO2, ZnO, ZrO2, AlN, TiN, metals such as Pt or Ir.

It comprises a remote microwave plasma generator, with adjustable 300-3000 W power, 2.45 GHz frequency, mounted to the loading chamber and connected to the reaction chamber. Up to twelve sources with six separate inlets may be used—seven if the plasma option is chosen. The precursor sources may comprise liquid, gaseous and/or solid chemicals. Precursors may also include ozone and/or plasma. The remote plasma option allows deposition of metals with a greatly reduced risk of short-circuiting and/or plasma damage. The processing temperature may in general be 50-500° C. Plasma may generally be used up to approximately 450° C., or up to approximately 650° C. with a heated sample holder.

It comprises a hot-wall and substantially separate inlets and instrumentation providing a relatively low particle (or substantially particle-free) processing adaptable on a wide range of materials on wafers, 3D objects, and nanoscale features. It provides a high degree of uniformity, even on porous, through-porous, high aspect ratio (up to 1:2500), and nanoparticle samples using their proprietary Picoflow™ diffusion enhancer. This enhancer provides a protective gas flow in an intermediate space to greatly reduce back-diffusion of the plasma species.

A suitable ALD process, for forming a monolayer comprising a first and second element, may comprise:

- loading a substrate as a sample into a reaction space;
- introducing a quantity of first molecules comprising the first element into the reaction space whereby at least a first portion of the first molecules adsorb to a surface of the substrate; and
- introducing a quantity of second molecules comprising the second element into the reaction space whereby at least a second portion of the second molecules reacts with the first portion on the surface of the substrate to form a monolayer of a compound comprising the first and second element.

Using the Picohot™ source system (PH-300) and Pico-Solution options for the R-200 Advanced, precursors were vaporized from stainless-steel precursor bottles at increased temperature and at room temperature. The Picohot™ 300 source system allows source heating up to 300 degr. C., and is suggested by the manufacturer to be suitable with source chemicals having a vapor pressure of at least 2 mbar at source temperature. The Picosolution™ 600 source system allows liquid precursors to be used, and are suggested by the manufacturer to be suitable with source chemicals having a vapor pressure of at least 10 mbar at source temperature.

Thermal ALD-processes at 200 degr. C were applied with layer-by-layer deposition method where the two different precursor materials (separated by N2 purge to remove surplus molecules from the reaction space) were used to build up a HfO2 (hafnium dioxide) coating 530—this is depicted in FIG. 3 as a coating 530 substantially covering the external surfaces of the substrate 430, 435 and the IDC sensors 230.

An optional stabilization time of approximately 90 minutes was used at 200 degr. C. Ten layers of approximately 5 nm were applied to provide an ALD layer of approximately 50 nm.

It is believed that ALD may be advantageous to create an ultra-thin conformal coating with low defects and/or reduced pinhole formation. Also, the deposition temperature for ALD may be kept below 200° C. which is advantageous for devices incorporating sensitive metallization and/or polymers.

3) PDMS Encapsulation

Samples were encapsulated with a layer comprising a substantially biocompatible PDMS (MED2-6215, NuSil Carpinteria, USA) 330.

From nusil.com/product/med-6215_optically-clear-low-consistency-silicone-elastomer:

MED-6215 is an optically clear, low consistency silicone elastomer. It is provided as two-parts which are solvent free and have a relatively low viscosity. It cures with heat via addition-cure chemistry. The mix ratio is 10:1 (Part A:Part B).

MED-6215 is considered substantially biocompatible—the manufacturer suggests that it may be used in human implantation for a period of greater than 29 days.

Uncured:

| Typical properties | Average Result | Standard | Nusil Test (NT-TM) |
|---|---|---|---|
| Appearance | Translucent | ASTM D2090 | 002 |
| Viscosity, Part A | 5,500 cP (5,500 mPas) | ASTM D1084, D2196 | 001 |
| Viscosity, Part B | 95 cP (95 mPas) | ASTM D1084 D2196 | 001 |
| Work Time | 5 hours | — | 008 |

Cured: 15 Minutes at 150° C. (302° F.)

| Typical properties | Average Result | Standard | Nusil Test (NT-TM) |
|---|---|---|---|
| Specific Gravity | 1.03 | ASTM D792 | 003 |
| Durometer, Type A | 50 | ASTM D2240 | 006 |
| Tensile Strength | 1,250 psi (8.6 MPa) | ASTM D412 | 007 |
| Elongation | 100% | ASTM D412 | 007 |
| Tissue Culture (Cytotoxicity Testing) | Pass | USP ISO 10993-5 | 061 |
| Elemental Analysis of Trace Metals | Pass | ASTM E305 | 131 |

| Property | Average Result |
|---|---|
| Durometer | 50 Type A |
| Viscosity | 3,800 MPa*s (3800 cP) |
| Work Time | 5 hours |
| Tensile | 8.62 MPa (1250 psi) |
| Appearance | Transparent |
| Cure | 15 minutes/150° C. |
| Cure System | Platinum |
| Elongation | 100% |
| Mix Ratio | 10:1 |
| Specific Gravity | 1.03 |
| Tack Free Time | 16 hours |
| Comment | Clear, 1.41 R.I. |

The manufacturer suggests silicone primer Nu-Sil MED1-161 as a primer to further improve adhesion of MED-6215 to various substrates including: metals (such as stainless steel, steel, copper and aluminum), ceramic materials, rigid plastics, and other silicone materials.

MED-6215 is available in medical grade—in other words, substantially biocompatible and suitable for use in a medical implantable device. This is realized by ensuring all raw materials, intermediates, and finished products (for Medical Grade) are manufactured with applicable GMP and/or appropriate regulatory standards: cGMP 21 CFR § 820 (Device), cGMP 21 CFR § 210-211 (Drug/API) and ISO 9001.

A dip-coating process was used for the encapsulation. The average relatively low viscosity, for example, 4000 to 7000 cP (mPas), appears to have allowed the PDMS to more easily flow over the sample. The thickness of the PDMS 330 was estimated to be between 50 and 200 μm (micron).

B. Experimental Set-Up

The lifetime reliability of ALD coatings may depend on factors such as the conformality and adhesion of the layer, and its stability in ionic media. This was measured using the IDC's impedance after an extended soak test.

Extended soaking used phosphate buffered saline (PBS) at approximately room temperature (approx. 23° C.).

Electrochemical impedance spectrometry (EIS) was carried out to evaluate the performance of the ALD and ALD-PDMS coatings using the methods described in "Apparatus to investigate the insulation impedance and accelerated life-testing of neural interfaces". Donaldson, Lamont, Shah Idil, Mentink, Perkins. J. Neural Eng. 2018, 10.1088/1741-2552/aadeac.

Measurements used a Solartron Modulab with a potentiostat in combination with a frequency response analyzer. Measurements were performed in a two-cell electrode configuration between the combs of the IDC structure. A Faraday cage was also used.

III. Results and Discussion

A. Measurement Results

After sample preparation and submersion in saline. EIS measurements were performed.

Figure 4A:
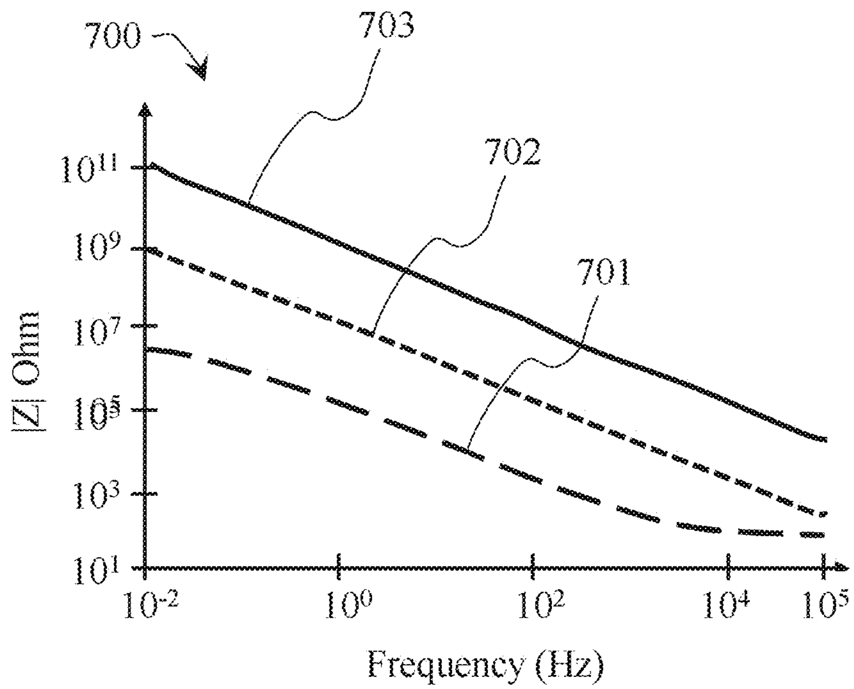
FIGS. 4A and 4B depict Electrochemical Impedance Spectroscopy (EIS) as Bode plot results of FIG. 4A; impedance magnitude and FIG. 4B; phase angle for three samples.
Figure 4B:
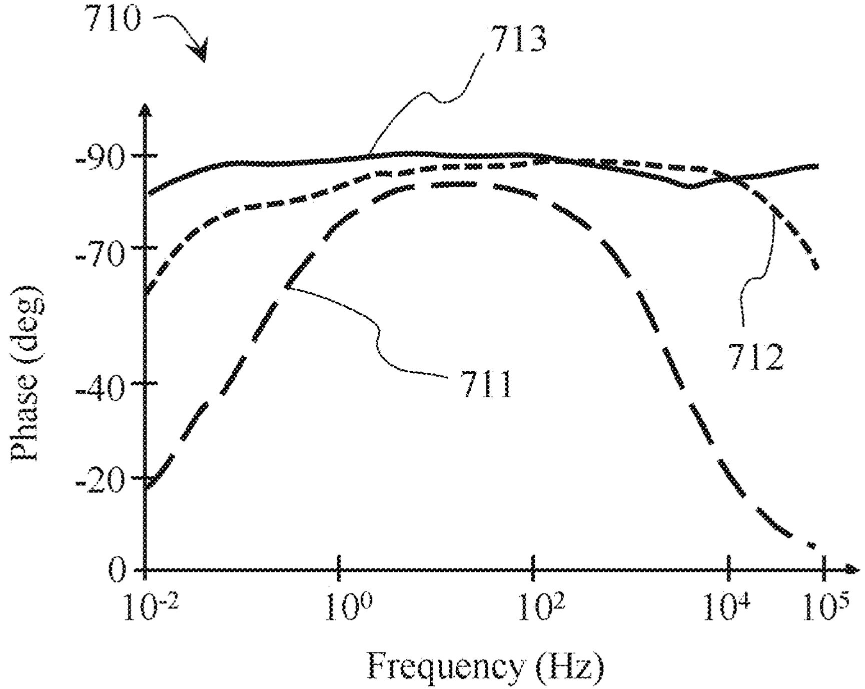

FIGS. 4A and 4B show the EIS results 700, 710 for three samples.

FIG. 4A depicts Bode plots 700, with impedance magnitude along the vertical (Y) axis from $10^1$ to $10^{11}$ |Z| Ohm, and frequency along the horizontal (X) axis from $10^{-2}$ to $10^5$ Hz:

- a bare IDC with exposed Pt metal 701, forming an approximately straight line from approx. $10^{-2}$, $5\times10^6$ to $10^4$, $10^2$, followed by a further straight line to $10^5$, $10^2$;
- an IDC coated with HfO2 ALD 702, forming an approximately straight line from $10^{-2}$, $10^9$ to $10^5$, $10^3$ and
- an IDC coated with an ALD-PDMS bilayer 703, forming an approximately straight line from $10^{-2}$, $10^{11}$ to $10^5$, $10^5$.

FIG. 4B depicts Bode plots 710, with phase along the vertical (Y) axis from 0 to −90 degrees, and frequency along the horizontal (X) axis from $10^{-2}$ to $10^5$ Hz:

- a bare IDC with exposed Pt metal 711, forming a curve passing through $10^{-2}$, −20 to $10^0$, −70 to $10^2$, −80 to $10^{-4}$, −20 to $10^{-5}$, 0;
- an IDC coated with HfO2 ALD 712, forming a curve passing through $10^{-2}$, −60 to $10^0$, −80 to $10^2$, −90 to $10^{-4}$, −80 to $10^{-5}$, −70; and
- an IDC coated with an ALD-PDMS bilayer 713, forming a curve passing through $10^{-2}$, −80 to $10^0$, −90 to $10^2$, −90 to $10^{-4}$, −80 to $10^{-5}$, −90.

For the bare IDC 701, 711, in the middle frequency band ($10^0$ Hz-$10^3$ Hz), the phase 711 appears to be relatively constant at approximately −80 degr. At lower frequencies (approx. $10^{-2}$ Hz), the polarization resistance appears to be dominant, resulting in a phase of approximately −20 degr. It is believed that this indicates the metal fully exposed to an electrolyte.

The ALD-coated IDC 702, 712, appeared to show relatively higher impedance values—this suggests a more capacitive behavior across the frequency range. This capacitance is believed to be caused by the Pt metal and electrolyte being separated by an ALD layer, which acts as a dielectric. It is believed that a fully conformal coating on the metal, or high resistance to fluid ingress, would result in a substantially capacitive behavior in the EIS results 700, 710.

For the ALD—PDMS bilayer 703, 713, the impedance 703 and phase 713 results show a substantially capacitive behavior across substantially the whole frequency range, with phase results 713 close to approximately −90°.

It is believed that any delamination or cracking of the ALD layer may expose more metal to the electrolyte, possibly resulting in a substantially lower impedance and phase angle that is more significantly seen in the lower frequency regions <$10^{-1}$ Hz. In FIGS. 4A and 4B, a comparison between the ALD 702, 712 and ALD-PDMS bilayer 703, 713 shows an approximately two orders of magnitude higher impedance value 703 for the bilayer encapsulated IDC 703, 713. Furthermore, the phase results 713 show a substantially more capacitive behavior.

Additionally, metal areas exposed due to ALD defects are also encapsulated with the PDMS, with a specific resistance of approximately $10^{15}$ Ohm·cm. It is believed that any significant delamination of the PDMS from ALD would allow water condensation, resulting in one or more conductive paths between the combs. This may result in a lower impedance and phase angle more significantly seen in the lower frequency regions of approximately <$10^{-1}$ Hz.

To track changes in the encapsulation and adhesion performance, monthly EIS measurements were done on all samples. The impedance and phase angle at approximately $10^{-2}$ Hz were selected as the reference value to monitor over time.

Figure 4C:
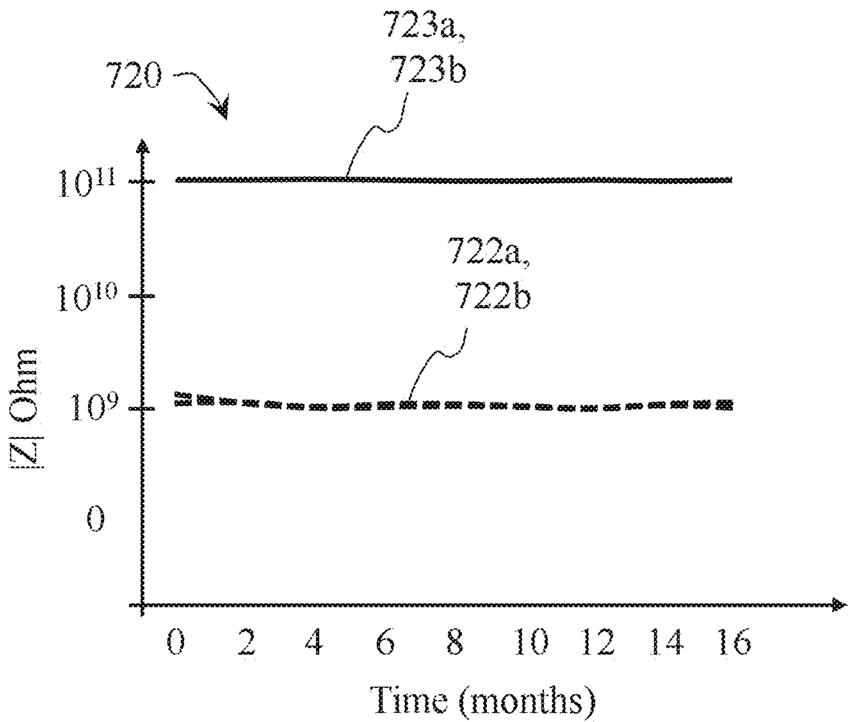
FIGS. 4C and 4D depict EIS results at $10^{-2}$ Hz over four hundred and fifty days of soaking as FIG. 4C; impedance magnitude and FIG. 4D; phase angle for four samples.
Figure 4D:
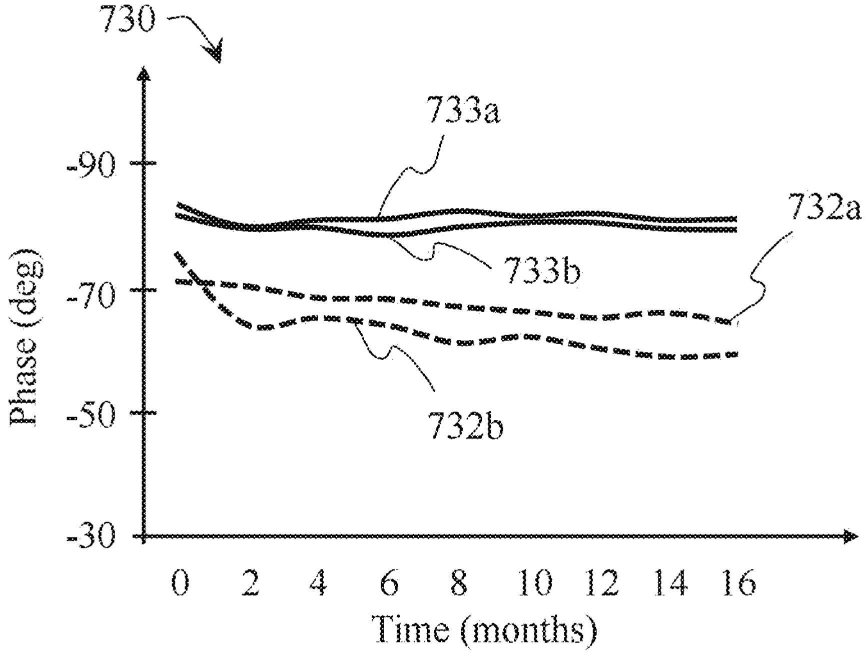

FIGS. 4C and 4D show the adhesion evaluation results 720, 730 for two ALD samples and two ALD-PDMS samples over the four hundred and fifty days of soaking. The results depicted in FIGS. 4A and 4B were considered as the values measured at T=0 days.

FIG. 4C depicts adhesion evaluation 720, with impedance magnitude along the vertical (Y) axis from 0 to $10^{11}$ |Z| Ohm, and Time along the horizontal (X) axis from 0 to 16 months:

- two IDC's coated with HfO2 ALD 722*a*, 722*b*, forming an approximately straight line from 0, $10^9$ to 16, $10^9$. Both samples provided substantially the same results, resulting in lines that are substantially overlapping, except for minimal deviations at 0 to 1 months, and 15 to 16 months; and
- two IDC's coated with an ALD-PDMS bilayer 723*a*, 723*b*, forming an approximately straight line from 0, $10^{11}$ to 16, $10^{11}$. Both samples provided substantially the same results, resulting in lines that are substantially overlapping.

FIG. 4D depicts adhesive evaluation 730, with phase along the vertical (Y) axis from −30 to −90 degrees, and Time along the horizontal (X) axis from 0 to 16 months:

- a first IDC 732*a* coated with HfO2 ALD, forming an approximately straight line from 0, −70 to 16, −65;
- a second IDC 732*b* coated with HfO2 ALD, forming an approximately straight line from 0, −75 to 2, −63 to 4, −65 to 16, 60;
- a first IDC 733*a* coated with an ALD-PDMS bilayer, forming an approximately straight line from 0, −83 to 2, −78 to 6, −80 to 16, −80; and
- a second IDC 733*b* coated with an ALD-PDMS bilayer, forming an approximately straight line from 0, −80 to 2, −78 to 6, −77 to 10, −80 to 16, −78.

For the ALD-only samples 722, 732, a drop in the phase angle 732*a*, 732*b* was measured after the first month of soaking, suggesting that fluid came into contact with the metals through one or more defects in the ALD layer. Substantially stable results were observed during the extended soaking. This is believed to indicate a substantially high stability of the HfO2 adhesion layer in ionic media and a substantially high degree of adhesion of HfO2 to Pt over an extended period of time. Significant deterioration of the HfO2 layer would be expected to show a relatively higher capacitive behavior, such as a significant drop in the impedance magnitude 720—this was not observed. Additionally, any significant delamination of the ALD layer from Pt would be expected to result in a substantially more resistive behavior, originating from the metal being exposed to saline—this was also not observed.

Optical inspections of the ALD samples 722, 732 supported these conclusions as no significant layer discoloration or degradation were observed.

For the ALD-PDMS bilayer samples 723, 733, substantially stable results were thus recorded over an extended period, suggesting a relatively high degree of adhesion between the two layers, and a substantially higher resistance to the ingress of fluids.

B. Conclusions

Pt is widely used as for conductors and/or electrode regions due to its high degree of biocompatibility and stability. However, long term stability may be reduced in conventional systems due to the relatively weak adhesion of encapsulants, such as PDMS, parylene and epoxy to Pt.

From the results, it is believed that adding an adhesion layer comprising one or more ceramic materials may be advantageous. In particular, an HfO2 ALD layer with an average thickness of approximately 25 nm to 100 nm, preferably approximately 50 nm, may provide a substantially stable intermediate adhesion layer between Pt and the PDMS. Additionally, a relatively high degree of adherence was also measured between the HfO2 layer and the SiO2 substrate—in particular between the Pt forks.

Where appropriate, a substrate comprising other materials may thus be provided with a layer of SiO2 and/or Pt to improve adhesion to the HfO2 ALD layer.

The ALD-PDMS bilayer of an encapsulation layer 330 and adhesion layer 530 appears particularly advantageous:

- the HfO2 ALD adhesion layer appeared to show a significantly higher stability in ionic media, thereby, providing relatively longer resistance against delamination or water permeation through the PDMS encapsulation.
- a PDMS having a relatively low average viscosity, for example 4000 to 7000 cP (mPas), for a significant time period during encapsulation, may further contribute to longer-lasting adhesion and defect reduction due to flowing of PDMS in-between any defects and openings in the ALD layer
- PDMS-type materials are, in general, highly suitable for implantation due to their relatively high degree of biocompatibility. By appropriate selection and processing, many PDMS-type materials may be configured and arranged to be substantially biocompatible.

Polymeric materials comprised in the substrate 400 are preferably selected for suitability to be flexible, and to comprise the one or more electrical conductors 210. Preferably, the polymeric substrate materials have a high degree of biocompatibility and durability. Suitable polymer materials, including LCP (Liquid Crystal Polymer) films, are described in "Polymers for Neural Implants", Hassler. Boretius, Stieglitz, Journal of Polymer Science: Part B Polymer Physics, 2011, 49, 18-33 (DOI 10.1002/polb.22169), In particular, Table 1 is included here as reference, depicting the properties of a polyimide (UBE U-Varnish-S). Parylene C (PCS Parylene C), a PDMS (NuSil MED-1000) similar to the PDMS polymers described above, SU-8 (MicroChem SU-8 2000 & 3000 Series), and an LCP (Vectra MT1300). A polyurethane may also be used.

Preferably, the first and/or second surface 410, 420 comprise a significant amount of one or more Liquid Crystal Polymers (LCP's). Optionally, the first and/or second surface 410, 420 may substantially consist of one or more LCP's. Optionally, the first and/or second surface 410, 420 may essentially consist of one or more LCP's.

LCP's are chemically and biologically stable thermoplastic polymers with relatively low moisture penetration properties. They are non-fibrous. Advantageously, LCP may be thermoformed allowing component covers with complex shapes to be provided.

At room temperature, thin LCP films have mechanical properties similar to steel. This is important as implantable devices 100, 101 must be strong enough to be implanted, strong enough to be removed (explanted) and strong enough to follow any movement of the neighboring anatomical features and/or structures without significant deterioration.

LCP belongs to the polymer materials with the lowest permeability for gases and water. LCP can be bonded to itself, allowing multilayer (two or more adjacent polymeric substrate layers) constructions with a substantially homogenous structure. A substrate 400 comprising two or more polymeric substrate layer may be modified (physically and/or chemically), such that it appears to be one layer of polymeric substrate. The table below compares several physical and chemical properties of a typical polyimide and a typical LCP.

| | Unit | LCP Flex | Polyimide Flex |
|---|---|---|---|
| Thickness | Um (micron) | 25, 50, 100 | 12, 25, 50 |
| Dielectric constant (10 GHz) | — | 2.9 | 3.2 |
| Dissipation factor (10 GHz) | — | 0.002 | 0.002 |
| Surface resistivity | ohm | 1.0E16 | 4.0E13 |
| Volume resistivity | Ohm cm | 1.0E18 | 2.6E14 |
| Dielectric strength | kV/mil | 3.5 | 7 |
| Young's modulus | GPa | 2.3 | 7.1 |
| Tensile strength | MPa | 280 | 220 |
| CTE, x-y | ppm/K | 18 | 20 |
| CTE, z | ppm/K | 200 | 120 |
| Solder float temperature | ° C. | >288 | >300 |
| Melting temperature/glass transition | ° C. | 330 | 343 |
| Moisture absorption (23° C., 24 h) | % | 0.04 | 1 |
| Flammability | — | UL 94 VTM-0 | UL 94 V0 |

In contrast to LCP, polyimides are thermoset polymers, which require adhesives for the construction of multilayer substrates. Polyimides are thermoset polymer material with high temperature and flexural endurance. LCP's are chemically and substantially biologically-stable thermoplastic polymers.

LCP may be used, for example, to provide multilayers with several layers of 25 um (micron) thickness. Optionally, the one or more electrical conductors 210 may be comprised in one or more interconnect layers. Such electrical interconnect layers may be provided by metallization of LCP on one or more surfaces using techniques from the PCB industry, such as metallization with copper. Electro-plating may also be used. If the substrate 400 is a multilayer, one or more electrical interconnections 210 may be comprised between adjacent polymeric substrate layers. The polymeric substrate layers may also be considered adjacent when one of more adhesion layers are used between them.

An electrical interconnection 210 in the context of this disclosure is not configured or arranged to be, in use, in contact with human or animal tissue. For example, by embedding the one or more interconnections 210 in one or more layers of a low conductance or insulating polymer, such as LCP.

Lamination may also be used to provide a substrate 400 with the desired physical and chemical properties, and/or to provide a convenient method of manufacture. For example, a substrate 400 may comprise three laminated polymer layers: two high temperature thermoplastic layers with a low-temperature layer in between, and high-temperature layers towards the outer surfaces.

In another example, two layers of silicone may be provided as polymeric substrate layers: a first layer of silicone is provided, metal is patterned on a surface of the first layer, and a second layer of silicone is added over the metal patterning by, for example, jetting, dispensing, over-moulding, and/or spin-coating.

Advantageously, the substrate, for example comprising an LCP, has a Young's modulus in the range 2500 to 3600 MPa (2.5 to 3.6 GPa).

Optionally, the substrate 400 may further comprise one or more electrical or electronic components configured to receive energy when electrical energy is applied to the one or more electrical conductors 210. For example, they may be inductively-coupled, capacitively-coupled or directly connected. This is particularly advantageous with substrates comprising significant amounts of one or more LCP's as PCB-techniques may be used. Preferably, a bio-compatible metal such as gold or platinum is used.

Preferably, one or more encapsulation layers 310, 320 and one or more adhesion layers 510, 520 are configured and arranged to resist the ingress of fluids to at least a portion of one or more surfaces 410, 420 proximate the one or more components.

For example, the one or more components may be an active component, a passive component, an electronic component, an integrated circuit (IC), an application-specific integrated circuit (ASIC), a field-programmable gate array (FPGA), an analog component, a digital component, a surface-mount device (SMD), a through-hole package, a chip carrier, a pin grid array, a fat package, a small outline package, a chip scale package, a ball grid array, a small-pin-count package, a flexible silicon device, a thin-film transistor (TFT), and any combination thereof.

The one or more electrical components may be configured and arranged to: resist, store charge, induct, sense, stimulate, amplify, process data, detect, measure, compare, switch, time, store data, count, oscillate, perform logic, add, generate stimulation pulses, and any combination thereof.

Conformable foil-like (or film-like) substrates 400 may be configured and arranged to follow the contours of underlying anatomical features very closely by being flexible. Very thin foil-like substrates 400 have the additional advantage that they have increased flexibility.

Advantageously, an LCP may be thermoformed allowing complex shapes to be provided. Very thin (and subsequently very conformable) and very flat (highly planar) layers of an LCP may be provided. For fine tuning of shapes, a suitable laser may also be used for cutting.

For example, a conformable foil-like substrate 400 comprising a significant amount of LCP may have a thickness in the range 50 microns (um) to 720 microns (um), preferably 100 microns (um) to 300 microns (um). For example, values of 150 um (micron), 100 um, 50 um, or um may be provided.

An implantable electrical device 100, 101 as described herein may be comprised in an implantable medical device 110. For example, such a medical device 110 may be configured and arranged to provide a degree of sensing, stimulation, data processing, detection or measurement, data storage, oscillation, logic performance, stimulation pulses generation, or any combination thereof.

As depicted in FIG. 2A, an improved implantable medical device 110 may be provided by modifying the implantable device 100, depicted in FIG. 1A. It is the same as the implantable electrical device 100 depicted in FIG. 1A, except in this cross-section:

- the substrate 400 comprises three protected surfaces, each surface being protected by a further adhesion layer 500 and a further encapsulation layer 300. The three protected surfaces comprise two opposite protected surfaces and a further adjacent surface;
- the extent of the further adhesion layer 500 is less than the extent of the substrate 400 for the two opposite protected surfaces. The extent of the further adhesion layer 500 is greater than the extent of the substrate 400 for the third adjacent protected surface;
- the extent of the further encapsulation layer 300 is less than the extent of the substrate 400 for the two opposite protected surfaces. The extent of the further encapsulation layer 300 is greater than the extent of the substrate 400 for the third adjacent protected surface; and
- the extent of the further adhesion layer 500 is less than the extent of the further encapsulation layer 300 for each protected surface.

Functionally, it may also be considered that the further encapsulation layer 300 comprises the first 310 and second 320 encapsulation layers depicted in FIG. 1B.

Functionally, it may also be considered that the further adhesion layer 500 comprises the first 510 and second 520 adhesion layers depicted in FIG. 1B.

However, the substrate 400 depicted in FIG. 2A, comprises a further protected surface, adjacent to such a protected first or second surface.

The further encapsulation layer 300 of FIG. 2A may be substantially identical, similar to a high degree or substantially different to the first encapsulation layer 310 depicted in FIG. 1A or 1B. The further encapsulation layer 300 of FIG. 2A may be substantially identical, similar to a high degree or substantially different to the second encapsulation layer 320 depicted in FIG. 1B.

The further adhesion layer 500 of FIG. 2A may be substantially identical, similar to a high degree or substantially different to the first adhesion layer 510 depicted in FIG. 1A or 1B. The further adhesion layer 500 of FIG. 2A may be substantially identical, similar to a high degree or substantially different to the second adhesion layer 520 depicted in FIG. 1B.

The medical device 110 further comprises:

- one or more stimulation electrodes 220, configured and arranged to transmit energy to human or animal tissue when electrical energy is applied to the one or more electrical conductors 210. For example, they may be inductively-coupled, capacitively-coupled or directly connected. In the example depicted, the one or more stimulation electrodes 220 are directly connected to the one or more electrical conductors 210. In many neurostimulation applications, a plurality of electrodes 220 may be required.

Optionally or additionally, one or more sensors 230 may similarly be provided—such sensors 230 are configured to be provided electrical signals and/or data to the one or more electrical conductors 210. For example, they may be inductively-coupled, capacitively-coupled or directly connected. If a multilayer substrate with electrical interconnections is provided, a high degree of customization is possible. For example, allowing direct measurements of parameters relevant for operation, such as humidity, temperature, electrical resistance and electrical activity.

Typically with neural-stimulation electrodes, one or more electrodes 220 are configured and arranged to operate as a ground or return electrode—this may be one of the existing electrodes or one or more further electrodes.

The skilled person will realize that such a stimulation electrode 220 and/or a tissue sensor is preferably not completely covered by an encapsulation layer 300 and/or an adhesion layer 500 as a sufficiently high degree of electrical connection or exposure to the implant environment are required for their function. For example, at least part of a stimulation electrode 220 and/or tissue sensor is masked during the encapsulation process to provide a conductive surface towards tissue. Additionally or alternatively, portions of the device may not be encapsulated.

FIG. 2A depicts a device 110 where substantially all of a stimulation electrode 220 is substantially not covered. In addition, in this cross-section, a portion of the substrate 400 is substantially not covered, providing a device 110 with a substantially encapsulated portion, and a substantially unencapsulated portion with one or more electrodes 220.

The extent of the further adhesion layer 500 in this cross-section for the two opposite surfaces is less than the extent of the further encapsulation layer 300 for these surfaces—this may be advantageous as the edges of the further adhesion layer 500 are at least partially encapsulated 300.

Applying this encapsulation to implantable stimulators generally provides a substantially unencapsulated portion with one or more electrodes 220, and a substantially encapsulated portion comprising a pulse generator and/or electronics.

FIG. 2B depicts a further embodiment of a medical device 111. More particularly, it depicts a cross-section through a portion of the substrate 400 comprising one or more electrode 220. The further medical device 111 is the same as the device 110 depicted in FIG. 2A except, in general, in this cross-section:

- the substrate 400 comprises four protected surfaces, each surface being protected by a further adhesion layer 500 and a further encapsulation layer 300;
- the extent of the further adhesion layer 500 is larger than the extent of substrate 400 for each protected surface;
- the extent of the further encapsulation layer 300 is larger than the extent of the substrate 400 for each protected surface; and
- the extent of the further adhesion layer 500 is less than the extent of the encapsulation layer 300 for each protected surface.

In this cross-section, “a part” of the one or more stimulation electrodes 220 is not completely covered to allow electrical connection or exposure to the implant environment after implantation. So, in the regions close to the stimulation electrodes 220, the general statements made above do not all apply completely. In particular, in this cross-section:

- the further adhesion layer 500 has been applied to the surface of the substrate 400 adjacent to the stimulation electrodes 220 and also applied to edge portions of the surface of the electrodes 220. This may provide additional protection against ingress at any interface between the electrode 220 and the substrate 400; and
- the further encapsulation layer 300 has been applied to the surface of the substrate 400 adjacent to the stimulation electrodes 220. However, is not significantly applied to edge portions of the surface of the electrodes 220.

In other words, in this cross-section at the edge portions of the surface of the electrodes 220, the extent of the further adhesion layer 500 is approximately the same as the extent of the further encapsulation layer 300.

This may be advantageous in certain configurations as the surface area of further encapsulation layer 300 in direct contact with the surface of the electrodes 220 is greatly reduced. In some cases, this surface area may be substantially zero.

Optionally, it may be advantageous if the extent of the further encapsulation layer 300 in this cross-section at an edge portion of one or more electrodes 220 is greater than the extent of the further adhesion layer 500—in some configurations, this may be advantageous as the edges of the further adhesion layer 500 are at least partially encapsulated 300.

So, the one or more stimulation electrodes 220 and/or sensor are preferably comprised in a surface, configured and arranged to provide a tissue interface.

“Comprised in a surface” means that the electrodes 220 are relatively thin (for example, when the substrate conforms to a substantially planar surface, having an extent along a transverse axis, approximately perpendicular to a longitudinal axis of the substrate, of 20 to 50 microns or less. Thinner electrodes may also be used to further increase the degree of conformability, for example 1 micron or less), and attached to (or at least partially embedded in) the surface.

This is particularly advantageous with substrates comprising significant amounts of one or more LCP’s as PCB/metallization-techniques may be used to provide conductive regions, which may be configured and arranged to be electrodes 220 and/or sensors 230. Preferably, a conductive material is used such as gold, platinum, platinum black, TiN, $IrO_2$, iridium, and/or platinum/iridium alloys and/or oxides. Conductive polymers, such as Pedot, may also be used. Preferably, bio-compatible conductive materials are used.

Thicker metal layers are generally preferred over thinner metal layers for electrodes 220 because they can be subjected to bodily substances that may dissolve the metal. However, thicker metal layers typically increase rigidity (reduce conformability) proximate the thicker layer.

In a second set of experiments, adhesion of PDMS MED2-4213 from NuSil to an LCP substrate was investigated using two different substrates and two different PDMS casting processes.

Different methods were used to evaluate the adhesion: adhesion evaluation by Peel-test dry, after PBS soaking at 60 degr. C. and a Peel-test based on ASTM D1876.

From nusil.com/product/med2-4213_fast-cure-silicone-adhesive:

MED2-4213 is a two-part, translucent, thixotropic, a relatively high extrusion rate, a relatively high tear strength, a relatively fast-cure silicone adhesive. It is also substantially free of tin (Sn), reducing the requirement for atmospheric moisture to cure. It also does not comprise significant amounts of curing byproducts, such as acetic acid or methyl alcohol.

MED2-4213 is considered substantially biocompatible—the manufacturer suggests that it may be used in human implantation for a period of greater than 29 days. Typical chemical and physical properties include:

Uncured:

| Typical properties | Result | Standard | Nusil Test Method |
|---|---|---|---|
| Appearance | Translucent | ASTM D2090 | 002 |
| Viscosity, Part A | 80000 cP (80000 mPas) | ASTM D1084, D2196 | 001 |
| Work Time | 15 hours minimum | — | 008 |

Cured: 15 Minutes at 150° C.

| Typical properties | Result | Standard | Nusil Test Method |
|---|---|---|---|
| Specific Gravity | 1.12 | ASTM D792 | 003 |
| Durometer, Type A | 15 | ASTM D2240 | 006 |
| Tensile Strength | 1,000 psi (6.9 MPa) | ASTM D412 | 007 |
| Elongation | 800% | ASTM D412 | 007 |
| Tear Strength | 130 ppi (23.0 kN/m) | ASTM D624 | 009 |

| Property | Average Result |
|---|---|
| Durometer | 15 Type A |
| Viscosity | 80,000 MPa*s (80000 cP) |
| Work Time | 15 hours |
| Tensile | 6.9 MPa (1000 psi) |
| Appearance | Translucent |
| Cure | 15 minutes/150° C. |
| Cure System | Platinum |
| Elongation | 800% |
| Mix Ratio | 1:1 |
| Specific Gravity | 1.12 |
| Rheology | Thixotropic/non-slump |
| Tear | 22.93 kN/m (130 ppi) |

It may be advantageous if the first (310) and/or second (320) encapsulation layers have/has a tensile strength in the range 6 to 8 MPa.

NuSil suggests that in many bonding applications (for a substrate comprising Aluminum. Glass, PMMA, Silicone) the use of a silicone primer to improve suitable adhesion is not required.

Use of a primer is suggested by the manufacturer when adhering to substrates comprising Polyetherimide, PEEK, Plastic, Polycarbonate. Polyimide, Polysulphone, Polyurethane, and Stainless steel.

In order to study the adhesion properties of the PDMS on LCP with different processing methods and adhesion layers, two different test substrates were used:

TYPE 1: an LCP 3-layered substrate with ALD coating on one side

TYPE 2: an LCP 2-layered laminated substrate with ALD coating on one side.

In general, it is advantageous to perform as few steps as possible when manufacturing an implantable electrical device—this may reduce the risk of introducing contamination or transport related issues, and it may reduce one or more costs.

A process with relatively few steps may be based around overmoulding electronics that are directly mounted on a substrate (here LCP). Depending on the hardware configuration, the PDMS used may need to adhere sufficiently well to surfaces such as:

an ASIC passivation layer in case of wire-bonding a Si-substrate in case of ASIC flip-chip or ACF mounting. Si-substrate is one of the relevant interfaces when using bare-die components. Bare die integrated circuits are often made from a wafer or substrate, that is a thin slice of crystalline silicon semiconductor. To make a bare-die component, this material undergoes many micro-fabrication processes to become an integrated circuit, but one side will always be the raw material that was used, most often crystalline silicon. Relevant interfaces include:

an ASIC interconnect

Gold from wire-bonds or stud bumps an ACF (Anisotropic conductive film), which is frequently epoxy based, with coated gold particles, for application of a bare-die component on bond-pads.

the substrate—in this case, a substrate comprising significant amounts of LCP.

TYPE 1 LCP substrates were prepared using one or more of the following process steps:

a) Providing a substrate: these substrates were substantially planar sheets of LCP with an average thickness of approximately 0.150 mm. The substrate comprised three layers; two 0.050 mm layers of ULTRALAM® 3908, separated by one 0.050 mm layer of ULTRALAM 3850.

ULTRALAM® 3908 LCP is available from Rogers Corporation (www.rogerscorp.com) and may be used as a bonding medium (adhesive layer) between copper, other LCP materials and/or dielectric materials. It is characterized by low and stable dielectric constant. It has a relatively low modulus, allowing relatively easy bending for flex applications, and relatively low moisture absorption.

It may be used with one or more layers of ULTRALAM® 3850 LCP to create substantially adhesive-less substantially all-LCP multi-layer substrates.

Typical values for physical and chemical properties of ULTRALAM® 3908 LCP include:

Mechanical Properties

| | Typical value | Units | Test Methods |
|---|---|---|---|
| Dimensional Stability | MD: <0.1<br>CMD: <0.1 | % | IPC 2.2.4<br>method A |
| Initiation Tear Strength, min | 1.4 (3.1) | Kg (lbs) | IPC 2.4.16 |
| Tensile Strength | 216 (31) | MPa (Kpsi) | IPC 2.4.19 |
| Tensile Modulus | 2450 (355) | MPa (Kpsi) | IPC 2.4.19 |
| Thickness Variation | <+/−10 | % | ASTM-D374 |

Thermal Properties

| | Typical value | Units | Test Methods |
|---|---|---|---|
| Coefficient of Thermal Expansion, CTE (30° C. to 150° C.) | X: 17<br>Y: 17<br>Z: 150 | ppm/° C. | IPC 2.4.41.3 |
| Solder Float, Method B (288° C.) | PASS | | IPC 2.4.13 |
| Thermal Conductivity @ 50° C. | 0.20 | W/m/° K | ASTM D5470 |
| Melting Temperature | 280 | ° C. | DSC |
| Relative Thermal Index (RTI) mechanical | 190 | ° C. | |
| electrical | 240 | ° C. | |

Electrical Properties

| | Typical value | Units | Test Methods |
|---|---|---|---|
| Dielectric Constant (10 GHz, 23° C.) | 2.9 | | IPC 2.5.5.5.1 |
| Dissipation Factor (10 GHz, 23° C.) | 0.0025 | | IPC 2.5.5.5.1 |
| Surface Resistivity | $1.2 \times 10^{12}$ | Mega Ohms | IPC 2.5.17 |
| Volume Resistivity | $2.6 \times 10^{14}$ | Mega Ohms-cm | IPC 2.5.17 |
| Dielectric Breakdown Strength | 118 (3000) | KV/cm (V/mil) | ASTM-D-149 |

Environmental Properties

| | Typical value | Units | Test Methods |
|---|---|---|---|
| Chemical Resistance | 98.7 | % | IPC 2.3.4.2 |
| Water Absorption (23° C., 24 hrs) | 0.04 | % | IPC 2.6.2 |
| Coefficient of Hydroscopic Expansion, CHE (60° C.) | 4 | ppm/% RH | 60° C. |
| Flammability | VTM-O | | UL-94 |

ULTRALAM® 3850 is available from Rogers Corporation (www.rogerscorp.com) and is a relatively high-temperature resistant LCP. It may be provided as a double copper clad laminate for use as laminate circuit materials.

The manufacturer suggests these products for use as a single layer or a multilayer substrate. ULTRALAM 3850 circuit materials are characterized by a relatively low and stable dielectric constant, and dielectric loss. It has a relatively low modulus, allowing relatively easy bending for flex applications, and relatively low moisture absorption.

It may be used with one or more layers of ULTRALAM® 3908 LCP to create substantially adhesive-less substantially all-LCP multi-layer substrates.

Typical values for physical and chemical properties of ULTRALAM® 3850 LCP include:

Mechanical Properties

| | Typical value | Units | Test Methods |
|---|---|---|---|
| Dimensional Stability | MD: −0.06 CMD: −0.03 | % | IPC 2.2.4 method B |
| Peel Strength | 0.95 (8.52) | N/mm (lbs/in) | IPC 2.4.8 (½ oz. ED foil) |
| Initiation Tear Strength, min | 1.4 (3.1) | Kg (lbs) | IPC 2.4.16 |
| Tensile Strength | 200 (29) | MPa (Kpsi) | IPC 2.4.16 |
| Tensile Modulus | 2255 (327) | MPa (Kpsi) | IPC 2.4.19 |
| Density | 1.4 | gm/cm3, Typical | |

Thermal Properties

| | Typical value | Units | Test Methods |
|---|---|---|---|
| Coefficient of Thermal Expansion, CTE (30° C. to 150° C.) | X: 17 Y: 17 Z: 150 | ppm/° C. | IPC 2.4.41.3 |
| Solder Float, Method B (288° C.) | PASS | | IPC 2.4.13 |
| Melting Temperature | 315 | ° C. (Typical) | DSC |
| Relative Thermal Index | | | |
| (RTI) mechanical | 190 | ° C. | |
| electrical | 240 | ° C. | |
| Thermal Conductivity @ 50° C. | 0.2 | W/m/° K | ASTM C518 |
| Thermal Coefficient of εr, −50° C. to 150° C. | (+)24 | ppm/° C. | IPC 2.5.5.5, 8 GHz |

Electrical Properties

| | Typical value | Units | Test Methods |
|---|---|---|---|
| Dielectric Constant, 10 GHz, 23° C. (Process) | 2.9 | | IPC 2.5.5.5.1 |
| Dielectric Constant, 10 GHz, 23° C. (Design) | 3.14 | | Differential Phase Length Method |
| Dissipation Factor (10 GHz, 23° C.) | 0.0025 | | IPC 2.5.5.5.1 |
| Surface Resistivity | $1 \times 10^{10}$ | Mega Ohms | IPC 2.5.17 |
| Volume Resistivity | $1 \times 10^{12}$ | Mega Ohms-cm | IPC 2.5.17 |
| Dielectric Breakdown Strength | 1378 (3500) | KV/cm (V/mil) | ASTM-D-149 |

Environmental Properties

| | Typical value | Units | Test Methods |
|---|---|---|---|
| Chemical Resistance | 98.7 | % | IPC 2.3.4.2 |
| Water Absorption (23° C., 24 hrs) | 0.04 | % | IPC 2.6.2 |
| Coefficient of Hydroscopic Expansion, CHE (60° C.) | 4 | ppm/% RH | 60° C. |
| Flammability | VTM-0 | | UL-94 |

Type 1 LCP Substrates were Further Prepared Using One or More of the Following Process Steps:

b1) an optional pre-cleaning of at least a portion of the substrate using IPA, followed by drying. Another suitable alcohol may also be used.

b2) Applying an adhesion coating: using ALD, a coating was applied to an outer surface of the substrate—in this case a surface comprising ULTRALAM® 3908 LCP. Ten alternating layers of approximately 5 nm Al2O3 and of approximately 5 nm HfO2, resulted in an approximately 100 nm multilayer. The extent of the ALD coating was approximately the same as the extent of the substrate. The ALD coating was applied using the PICOSUN® R-200 Advanced ALD reactor described above. It was applied at a temperature substantially lower than the melting temperature of the LCP. For these TYPE 1 LCP substrates, it was applied at approximately 125 degr C after an optional stabilization time of approximately 90 minutes.

For comparison, this step was omitted for some of the samples (in other words, the PDMS was applied directly to the LCP).

c) Cleaning at least a portion of the adhesion coating: as preparation for the PDMS coating, an optional ten-minute ozone (O3) plasma treatment was performed to clean the ALD surface. The PDMS was applied within fifteen minutes from the ozone cleaning. For comparison, some samples were not cleaned before the PDMS coating was applied UV O3 (ozone) plasma cleaning is suitable for dry, non-destructive atomic cleaning and removal of organic contaminants. It uses intense 185 nm and 254 nm ultraviolet light. In the presence of oxygen, the 185 line produces Ozone and while the 254 line excites organic molecules on the surface. This combination drives the rapid destruction and decimation of organic contaminants.

d) Applying an encapsulation coating: a PDMS coating of approximately 500 um to 1000 um of MED2-4213 was applied on top of the ALD coating. A syringe was filled with MED2-4213, and mixed & degassed at relatively high speed (2500 rpm) for three minutes. It was cured at 150 degr C for 10 min and post-cured at 80 degr C for 24 hours. The extent of the PDMS coating was less than the extent of the ALD coating, whereby the ALD coating was exposed (not covered by encapsulant) close to the edge of the substrate. After applying the PDMS on the substrate, the substrate was placed on the PTFE (polytetrafluorethylene)-coated pre-heated plate, and a weight was pressed on top of it.

So, six samples of TYPE 1 LCP were prepared:

| | Nr of samples | ALD coating | Cleaning | PDMS coating |
|---|---|---|---|---|
| 1.1 | Two | None | None | MED2-4213 |

-continued

| | Nr of samples | ALD coating | Cleaning | PDMS coating |
|---|---|---|---|---|
| 1.2 | Two | Ten x (5 nm Al2O3 + 5 nm HfO2) | None | MED2-4213 |
| 1.3 | Two | Ten x (5 nm Al2O3 + 5 nm HfO2) | O3-plasma (10 min) | MED2-4213 |

A Pass/Fail test was defined for the TYPE 1 LCP substrates by hand:

after curing the PDMS, a dry Peel-test was performed (no soaking) and the degree of delamination was noted after the dry Peel-test, the samples were soaked in a PBS solution at 60 degr C for 1 day, 1 week, and 4 weeks, and the Peel-test was repeated to determine a second degree of delamination.

Three degrees of delamination were defined:

Delamination: the PDMS can be removed relatively easily from the substrate

Partial delamination: the PDMS can be removed relatively easily in some areas, but sticks relatively well in other areas Adhesion: the PDMS does not substantially delaminate Phosphate-buffered saline (abbreviated PBS) is a buffer solution commonly used in biological research. It is a water-based salt solution containing disodium hydrogen phosphate, sodium chloride and, in some formulations, potassium chloride and potassium dihydrogen phosphate. The buffer helps to maintain a constant pH. The osmolarity and ion concentrations of the solutions are selected to match those of the human body (isotonic).

| Samples | Dry | Soak after 24 h @60° C. PBS | Soak after 1 week @60° C. PBS | Soak after 4 weeks @60° C. PBS |
|---|---|---|---|---|
| 1.1 | Delamination | Not applicable | Not applicable | Not applicable |
| 1.2 | Adhesion | Partial Delamination | Partial Delamination | Partial Delamination |
| 1.3 | Adhesion | Adhesion | Adhesion | Adhesion |

Samples 1.1: in general, PDMS has a low degree of adhesion to LCP

Samples 1.2: the PDMS could not be peeled from the surface in dry state. After twenty-four hours of soaking, part of the PDMS could be peeled from the substrate, although no moisture filled voids were observed. After peeling away some of the PDMS, the rest stuck so well to the substrate it could not be peeled off any further, not even after 1 or 2 weeks of additional soaking. It was suspected that the initial delamination was due to local contamination during PDMS processing or processing issues.

Samples 1.3: these samples showed good adhesion. No delamination was achieved in dry and wet conditions until after two weeks of testing.

Conclusions:

In general, PDMS had a low degree of adhesion to LCP without any adhesion layer (samples 1.1).

In samples 1.2 (coated with ALD and then encapsulated with PDMS without O3 cleaning), the PDMS could not be peeled from the surface in dry state. After 24 hours of soaking, part of the PDMS could be peeled from the substrate, although no moisture filled voids were observed. After peeling away some of the PDMS, the rest stuck so well to the substrate it could not be peeled off any further, not even after two weeks of additional soaking. Samples with a more conformal ALD multilayer showed good adhesion even after two weeks of soaking.

Samples 1.3 (coated with ALD and encapsulated with PDMS after an O3 cleaning step) showed the highest degree of adhesion. No substantial delamination was achieved in dry or wet conditions (after 2 weeks of soaking)

An Al2O3/HfO2 multilayer ALD layer with a total average thickness of approximately 50 nm to 200 nm, preferably approximately 100 nm, may provide an advantageous intermediate adhesion layer between LCP and the PDMS polymer.

Type 2 LCP Laminated Substrates were Prepared Using One or More of the Following Process Steps:

a) Providing a substrate: these substrates were laminated sheets of LCP, with an average thickness of approximately 0.110 mm. The substrate comprised four layers; one outer layer of copper connection pads, one 0.050 mm layer of ULTRALAM® 3850, one inner layer of one or more copper conductors, and one 0.025 mm layer of ULTRALAM 3908:

a1) an approximately 50 um-thick sheet of LCP ULTRALAM® 3850, clad on a first surface with a first copper layer. This first copper layer was approximately 18 um-thick. The first copper layer was configured and arranged to form copper connection pads, for example by masking and etching, which may be considered to be comprised in an outer surface of the laminated substrate;

a2) the ULTRALAM® 3850 was further clad with a further copper layer. This second layer was approximately 18 um-thick. Optionally, it may be configured and arranged to form one or more conductors, for example by masking and etching, which may be considered to be comprised in an inner surface of the laminated substrate. If no inner conductors are required, the further copper layer may be omitted or completely removed;

a3) an approximately 25 um-thick sheet of LCP ULTRALAM® 3908, bonded to the inner surface of the ULTRALAM® 3850 layer, and further bonded to the one or more conductors.

Optionally, the laminated sheets may be substantially planar.

b) Applying an adhesion coating:

b1) an optional pre-cleaning of at least a portion of the substrate using IPA, followed by drying. Another suitable alcohol may also be used.

b2) using ALD, a coating was applied to an outer surface of the substrate—in this case a surface comprising ULTRALAM® 3908 LCP. It was not the outer surface of the substrate comprising one or more connection pads. Ten alternating layers of approximately 5 nm Al2O3 and of approximately 5 nm HfO2 resulted in an approximately 10 nm multilayer. The ALD coating was applied using the PICOSUN® R-200 Advanced ALD reactor described above. It was applied at a temperature substantially lower than the melting temperature of the LCP. For these TYPE 1 LCP substrates, it was applied at approximately 125 degr C after an optional stabilization time of approximately 90 minutes. The extent of the ALD coating was approximately the same as the extent of the substrate.

b3) Applying an adhesion improver: MED-166 from NuSil is a specially formulated primer which is suggested by the manufacturer to improve adhesion of PDMS to various substrates including: rigid plastics, and other silicone materials. The manufacturer suggests that it is suitable for use in human implantation for a period of greater than 29 days.

c) Cleaning at least a portion of the adhesion coating before encapsulation:

c1) Option 1: cleaning using ethanol, followed by drying for 4 hours at 70° C. Another suitable alcohol may also be used.

c2) Option 2: exposing the ALD surface to a plasma comprising O2.

O2 (oxygen) plasma refers to any plasma treatment performed while actively introducing oxygen gas to the plasma chamber. Oxygen plasma is created by utilizing an oxygen source on a plasma system.

Additionally or alternatively, ozone (O3) may be used.

d) Applying an encapsulation coating:

d1) Applying an encapsulation mask to simplify testing: a strip of Kapton tape (10 mm wide) was applied to one edge to mask a small section to which the pull-tester is to be clamped during the Peel-test.

d2) Applying an encapsulation coating: a PDMS coating of approximately 500 um to 1000 um of MED2-4213 was applied on top of the ALD coating. Vacuum centrifugal casting at 100 degr. C used with PTFE-coated moulds under a relatively low vacuum, for example 800-900 Pa (8 to 9 mbar)-vacuum centrifugal casting was used to reduce the risk of air inclusion in the PDMS. In general, applying a vacuum may be advantageous in improving the application to an adhesion coating of the encapsulation of a PDMS having an average viscosity in the range 55000 to 100000 cP (mPas) for a significant time period.

The extent of the PDMS coating was approximately the same as the extent of the ALD coating. After removing the Kapton tape, a strip of approximately 10 mm wide was provided where the PDMS was not attached to the ALD coating.

e) Performing further processing: the coated substrate of approximately 100×75 mm area was cut into 7 pieces of approximately 100×10 mm for Peel-testing. Each piece had an area of approximately 10×10 mm without the PDMS coating at is edge due to Kapton tape removal.

So, fifteen samples of type (2) were prepared:

| | Nr of samples | ALD coating | Primer | Cleaning | PDMS coating |
|---|---|---|---|---|---|
| 2.1 | Three | None | | Ethanol | MED2-4213 |
| 2.2 | Three | None | MED-166 | Ethanol | MED2-4213 |
| 2.3 | Three | 10x (5 nm Al2O3 + 5 nm HfO2) | None | Ethanol | MED2-4213 |
| 2.4 | Three | None | None | O2 plasma treatment | MED2-4213 |
| 2.5 | Three | 10x (5 nm Al2O3 + 5 nm HfO2) | None | O2 plasma treatment | MED2-4213 |

Peel-test according to ASTM D1876 was adapted for testing the TYPE 2 LCP or laminated substrates). A Peel-tester was used to measure the lamination force.

4. Peel-Test Results

Figure 8:
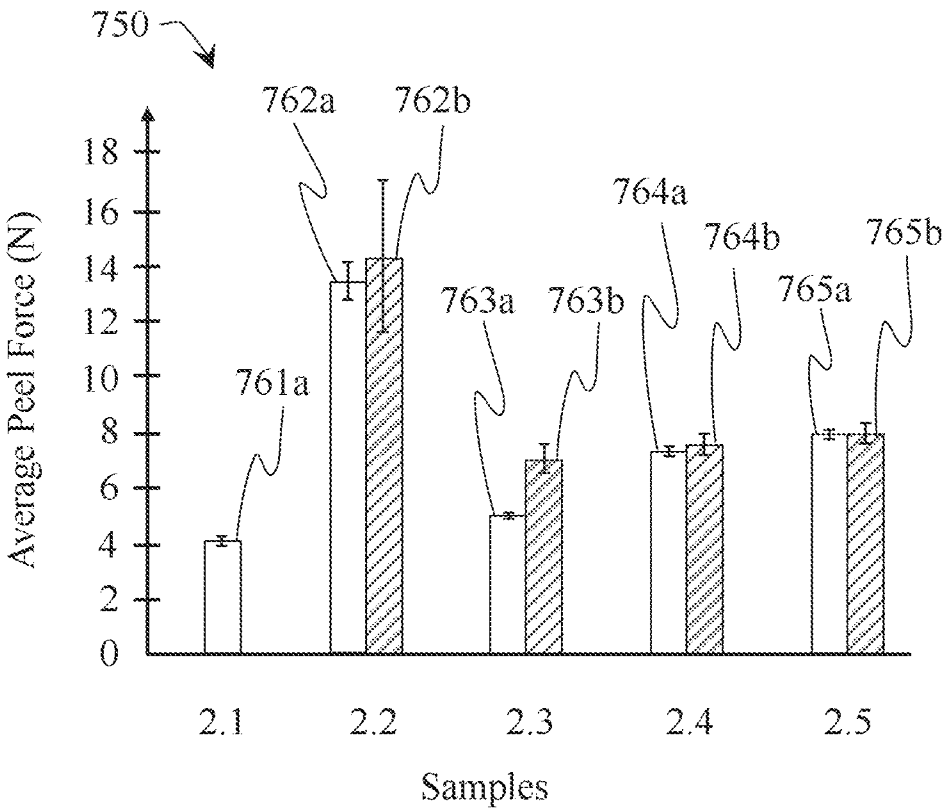
FIG. 8 compares the average pull force, dry and after soaking, of LCP coated with PDMS using different processes.

FIG. 8 depicts a graph 750 comparing the average pull force under dry (not soaked) conditions with the average pull forces after 24 hours of soaking at 60 degr. C in PBS. The samples of LCP were coated with PDMS using different processes.

Average peel force is plotted along the vertical (Y) axis from 0 to 18 N, and the results are indicated for the different samples along the horizontal (X) axis. To simplify interpretation, the order of the samples chosen is numerical: from left to right, samples 2.2, 2.2, 2.3, 2.4 and 2.5.

For each sample, the vertical length of each bar indicates the average peel force in Newtons (N). For each bar, an "I" shaped line is also depicted to indicate the variation measured in the pull force values used to determine the average. For each sample, an unfilled bar is depicted on the left-hand side showing the average pull force under dry conditions, and a hatched bar on the right-hand side showing the average pull force after 24 hours of soaking at 60 degr. C. in PBS.

For sample 2.1, an unfilled bar 761*a* is depicted of approx. 4N, with a relatively small degree of variation. No value after soaking is depicted.

For sample 2.2, an unfilled bar 762*a* is depicted of approx. 13N, with an average degree of variation. A hatched bar 762*b* is depicted of approx. 14N, with a relatively high degree of variation.

For sample 2.3, an unfilled bar 763*a* is depicted of approx. 5N, with a relatively small degree of variation. A hatched bar 763*b* is depicted of approx. 7N, with an average degree of variation.

For sample 2.4, an unfilled bar 764*a* is depicted of approx. 7N, with a relatively small degree of variation. A hatched bar 764*b* is depicted of approx. 7.5N, with an average degree of variation.

For sample 2.5, an unfilled bar 765*a* is depicted of approx. 8N, with a relatively small degree of variation. A hatched bar 765*b* is depicted of approx. 8N, with an average degree of variation.

The average peel forces measured were:

| Samples | Average Peel Force (N) - Dry | Average Peel Force (N) - After 24 hours soaking in PBS at 60 degr. C. |
|---|---|---|
| 2.1 | 4.05 (761a) | Not applicable |
| 2.2 | 13.38 (762a) | 14.22 (762b) |
| 2.3 | 5.23 (763a) | 7.29 (763b) |
| 2.4 | 7.31 (764a) | 7.56 (764b) |
| 2.5 | 8.31 (765a) | 8.32 (765b) |

It appears that a stable overmolding encapsulation process was achieved, showing substantially none, or very few, air bubbles in the PDMS. Substantial delamination of the LCP/PDMS interface was observed on 3 out of 7 samples directly after overmolding. For this reason, the Peel-test was applied to get a more qualitative measure of the adhesion strength.

Samples 2.1: without additional priming or cleaning, the PDMS had a very low degree (approx. 4N—761*a*) of adhesion to LCP.

Samples 2.2: substrates with a primer appeared to have a relatively high degree of adhesion (approx. 13N—762*a*—compared to approx. 4N—761*a*). During the test, some regions had a higher degree of adhesion, which resulted in the PDMS rupturing before peeling the samples completely. The average pull force after the soaking test appeared to be higher at approx. 14N—762*b*, but a relatively high degree of deviation was also observed.

- Samples 2.3: by adding an ALD multilayer, specifically the HfO2-Al2O3 multilayer ending with HfO2, the degree of dry adhesion appeared improved (from approx. 4N—761*a*—to approx. 5N—763*a*). The results under dry conditions—763*a*—appears to have a very low degree of deviation. The average pull force after the soaking test appeared to be higher at approx. 7N—763*b*.
- Samples 2.4: O2-plasma activation also appeared to increase the adhesion (approx. 7N—764*a*—compared to approx. 4N—761*a*). The average pull force after the soaking test appeared to be slightly higher at approx. 7.5N—764*b*.
- Samples 2.5: plasma activation appeared to further improve the degree of adhesion (approx. 8N—765*a*—compared to approx. 4N—761*a*). The average pull force after the soaking test appeared to be approximately the same at 8N—765*b*. A small increase in deviation—765*b*—was observed after soaking.

Conclusions:

A relatively high degree of adhesion was observed using a primer—for example, MED-166 from NuSil may be used. But it may be less-preferred in some uses. In particular, for implantable devices, it is advantageous to use materials that are significantly biocompatible and more preferably materials that are substantially biocompatible (have a high degree of biocompatibility). Although the manufacturer of MED-166 suggests that it is suitable for implantation for more than 29 days, primers are often epoxy adhesives which use volatile solvents. This may increase the risk of contamination due to insufficient evaporation and/or require additional process steps to ensure sufficient solvent removal.

In addition, for implantable devices, a high degree of quality control is often required to limit the risk of defects. Primers must typically be applied using a spray coating process, which may be difficult to perform with a high degree of reliability. It is believed that such reliability issues were the cause of the partial delamination observed.

- An Al2O3/HfO2 multilayer ALD layer with a total average thickness of approximately 50 nm to 200 nm, preferably approximately 100 nm, may provide an advantageous intermediate adhesion layer between LCP and the PDMS polymer. In general, a ceramic layer with a thickness of less than,
- the ALD coating used improved adhesion of PDMS to LCP using materials suitable for use in an implantable electrical device.
- the ALD multilayer stack not only improved the adhesion, but also improved the barrier property to protect a surface region against moisture ingress. This is preferred over a primer because the primer typically has a high degree of permeability for moisture.

Based upon the improved adhesion between a PDMS and surfaces comprising a significant amount of Pt, $SiO_2$ and an LCP, an adhesion layer comprising a ceramic material may be advantageously used for a wide range of substrate materials. In particular, adhesion of a PDMS may be improved where a first surface 410 and/or second surface 420 comprises a significant amount of a substance selected from the group comprising: a Liquid-Crystal Polymer (LCP), a polyimide. Parylene-C, SU-8, a polyurethane, or any combination thereof. These substances may be comprised in a flexible substrate.

Where appropriate, a substrate comprising other materials may thus be provided with a layer of such a material to improve adhesion to the HfO2 ALD layer.

The skilled person will also realise that adhesion may be improved by optionally or additionally applying a conformal coating to such a substrate, for example with an ALD process, applying a layer of SiO2 (silicon dioxide).

PDMS is, in general, a silicone rubber, with siloxane as the basic repeating unit. Methyl groups are substituted by a variety of other groups, for example, phenyl, vinyl or trifluoropropyl groups, depending on the type of PDMS, enabling the linkage of organic groups to an inorganic backbone.

Based upon the improved adhesion to a PDMS using one or more adhesion layers comprising HfO2 and/or Al2O3, an adhesion layer comprising a suitable ceramic material may be advantageously used for a wide range of substrate materials.

Suitable ceramic surfaces are relatively rich in hydroxyl groups. It is believed that the high degree of adhesions is due to oxygen in suitable PDMS-types can form strong bonds with the hydroxyl groups on the suitable ceramic surface. This may be chemical bonding, hydrogen-bridge bonding or some combination.

Suitable ceramics include:

- carbides, such as silicon carbide (SiC);
- oxides, such as aluminum oxide (Al2O3);
- nitrides, such as with silicon (SixNy or SiNxOy) and, in particular, silicon nitride (Si3N4); and
- many other materials, including the mixed oxide ceramics that can act as superconductors.

In particular, adhesion of a PDMS may be improved where the ceramic material is selected from the group comprising: HfO2, Al2O3, Ta2O3, TiO2, and any combination thereof.

It is also expected that Diamond-like carbon may be advantageously used to improve adhesion.

Adhesion may be further improved by activating the surface of the ceramic layer—for example, by applying an alcohol, in particular ethanol; using a plasma comprising O3 (Ozone) and/or comprising O2; treating with a silane; or any combination thereof.

An adhesion layer may be a bi-layer or multilayer, in which one or more layers may be configured and arranged for a relatively high degree of adhesion, and one or more layers may be configured and arranged for a relatively high degree of corrosion resistance (impermeability).

For example, it is believed that a layer comprising Al2O3 provides a relatively high degree of adhesion. For example, it is believed that a layer comprising HfO2 provides a relatively high degree of corrosion resistance.

Figure 5:
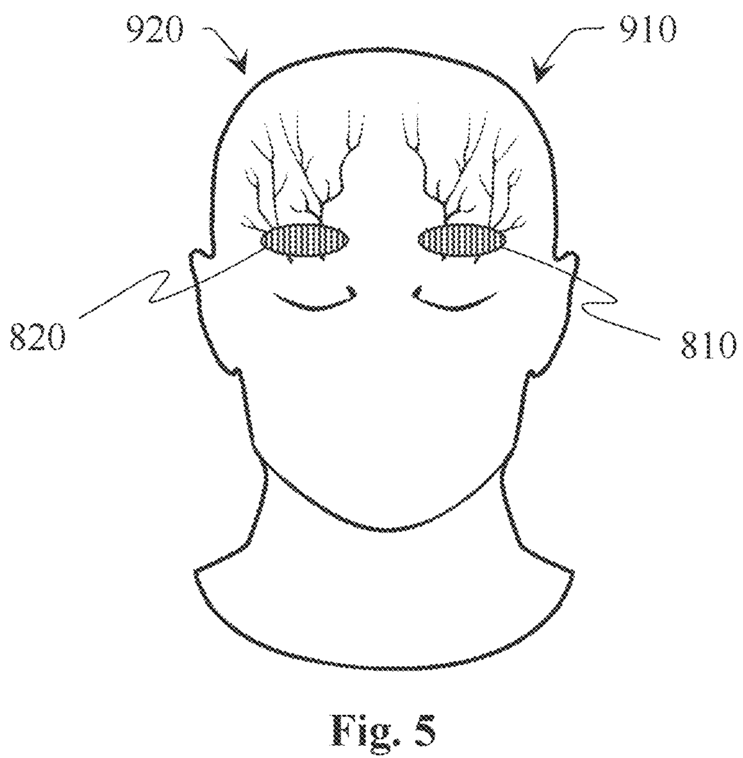
FIG. 5 and FIG. 6 depict examples of nerves that may be stimulated using an improved implantable medical device to treat headaches.
Figure 6:
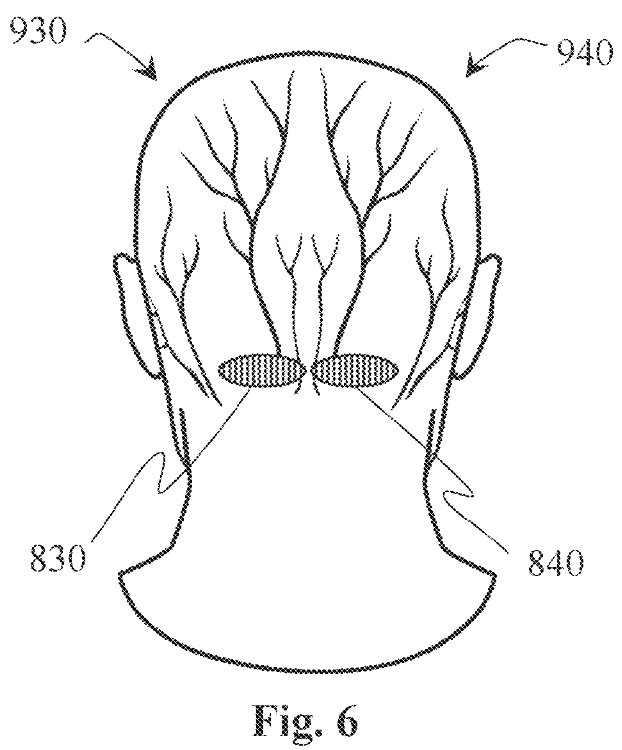

FIG. 5 and FIG. 6 depict examples of nerves that may be stimulated using one or more suitably configured improved medical devices 110, 111, configured to provide neurostimulation to treat, for example, headaches, chronic headaches or primary headaches. In particular, if the substrate is substantially flexible, it may conform better to the curved surfaces of the head and/or skull. This means that the comfort to the user of an implantable medical device 110, 111 may be increased.

FIG. 5 depicts the left supraorbital nerve 910 and right supraorbital nerve 920 which may be electrically stimulated using a suitably configured device. FIG. 6 depicts the left greater occipital nerve 930 and right greater occipital nerve 940 which may also be electrically stimulated using a suitably configured device.

Depending on the size of the region to be stimulated and the dimensions of the part of the device to be implanted, a suitable location is determined to provide the electrical stimulation required for the treatment. Approximate implant locations for the part of the stimulation device comprising stimulation electrodes are depicted as regions:

- location 810 for left supraorbital stimulation and location 820 for right supraorbital stimulation for treating chronic headache such as migraine and cluster.
- location 830 for left occipital stimulation and location 840 for right occipital stimulation for treating chronic headache such as migraine, cluster, and occipital neuralgia.

In many cases, these will be the approximate locations 810, 820, 830, 840 for the one or more implantable medical devices 110, 111.

For each implant location, 810, 820, 830, 840 a separate stimulation device 110, 111 may be used. Where implant locations 810, 820, 830, 840 are close together, or even overlapping a single stimulation device 110, 111 may be configured to stimulate at more than one implant location 810, 820, 830, 840.

A plurality of implantable medical devices 110, 111 may be operated separately, simultaneously, sequentially or any combination thereof to provide the required treatment.

Figure 7:
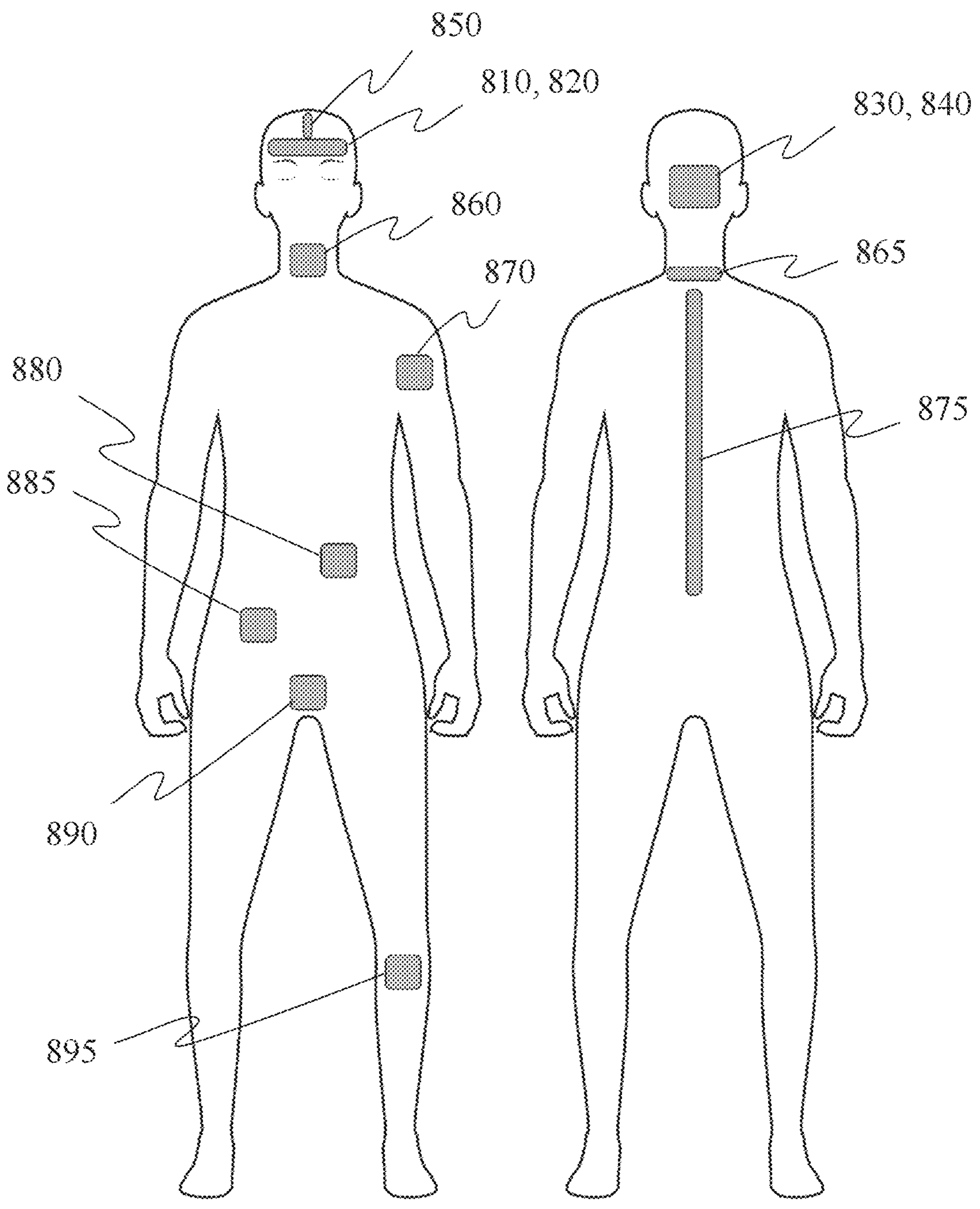
FIG. 7 depicts examples of nerves that may be stimulated for other treatments.

FIG. 7 depict further examples of nerves that may be stimulated using one or more suitably configured improved implantable medical devices 110, 111 to provide neurostimulation to treat other conditions. The locations depicted in FIG. 5 and FIG. 6 (810, 820, 830, 840) are also depicted in FIG. 7.

Depending on the size of the region to be stimulated and the dimensions of the part of the device to be implanted, a suitable location is determined to provide the electrical stimulation required for the treatment. Approximate implant locations for the part of the stimulation device comprising stimulation electrodes are depicted as regions:

- location 810 for cortical stimulation for treating epilepsy;
- location 850 for deep brain stimulation for tremor control treatment in Parkinson's disease patients; treating dystonia, obesity, essential tremor, depression, epilepsy, obsessive compulsive disorder, Alzheimer's, anxiety, bulimia, tinnitus, traumatic brain injury, Tourette's, sleep disorders, autism, bipolar; and stroke recovery
- location 860 for vagus nerve stimulation for treating epilepsy, depression, anxiety, bulimia, obesity, tinnitus, obsessive compulsive disorder and heart failure;
- location 860 for carotid artery or carotid sinus stimulation for treating hypertension;
- location 860 for hypoglossal & phrenic nerve stimulation for treating sleep apnea;
- location 865 for cerebral spinal cord stimulation for treating chronic neck pain;
- location 870 for peripheral nerve stimulation for treating limb pain, migraines, extremity pain;
- location 875 for spinal cord stimulation for treating chronic lower back pain, angina, asthma, pain in general;
- location 880 for gastric stimulation for treatment of obesity, bulimia, interstitial cystitis;
- location 885 for sacral & pudendal nerve stimulation for treatment of interstitial cystitis;
- location 885 for sacral nerve stimulation for treatment of urinary incontinence, fecal incontinence;
- location 890 for sacral neuromodulation for bladder control treatment; and
- location 895 for fibular nerve stimulation for treating gait or footdrop.

The descriptions thereof herein should not be understood to prescribe a fixed order of performing the method steps described herein. Rather the method steps may be performed in any order that is practicable. Similarly, the examples used to explain the algorithm are presented as non-limiting examples, and are not intended to represent the only implementations of these algorithms. The person skilled in the art will be able to conceive many different ways to achieve the same functionality as provided by the embodiments described herein.

For example, one or more features that improve conformance may be applied to embodiments that are configured and arranged for improved encapsulation. In some embodiments, it may be advantageous to apply features that improve encapsulation but reduce conformance.

For example, one or more features that improve encapsulation may be applied to embodiments that are configured and arranged for improved conformance. In some embodiments, it may be advantageous to apply features that improve conformance but reduce encapsulation.

Many types of implantable distal ends of stimulation devices are depicted. But this does not exclude that the rest of the device is implanted. This should be interpreted as meaning that at least the electrode section of the distal end is preferably configured and arranged to be implanted.

Although the present invention has been described in connection with specific exemplary embodiments, it should be understood that various changes, substitutions, and alterations apparent to those skilled in the art can be made to the disclosed embodiments without departing from the spirit and scope of the invention as set forth in the appended claims Although the present invention has been described in connection with specific exemplary embodiments, it should be understood that various changes, substitutions, and alterations apparent to those skilled in the art can be made to the disclosed embodiments without departing from the spirit and scope of the invention as set forth in the appended claims.

REFERENCE NUMBERS USED IN DRAWINGS

100, 101, 102 improved implantable electrical or electronic devices
110, 111 improved implantable medical devices
130 a test substrate
210 one or more electrical conductor
220 one or more stimulation electrodes
230 one or more sensors
300 a further biocompatible encapsulation layer
310 a first biocompatible encapsulation layer
320 a second biocompatible encapsulation layer
330 a third biocompatible encapsulation layer
400 a substrate
430 a silicon substrate
435 a $SiO_2$ (silicon dioxide) layer
410 a first surface
420 a second surface
500 a further adhesion layer
510 a first adhesion layer
520 a second adhesion layer
530 a third adhesion layer
700 Bode plots presented as impedance magnitude
701 Impedance magnitude for a bare IDC with exposed Pt metal

702 Impedance magnitude for an IDC coated with HfO2 ALD

703 Impedance magnitude for an IDC coated with an ALD-PDMS bilayer

710 Bode plots presented as phase angle

711 Phase angle for a bare IDC with exposed Pt metal

712 Phase angle for an IDC coated with HfO2 ALD

713 Phase angle for an IDC coated with an ALD-PDMS bilayer

720 Adhesion monthly performance presented as impedance magnitude

722*a*, 722*b* Impedance magnitude for IDC's coated with HfO2 ALD

723*a*, 723*b* Impedance magnitude for IDC's coated with an ALD-PDMS bilayer

730 Adhesion monthly performance presented as phase angle

732*a*, 732*b* Phase angle for IDC's coated with HfO2 ALD

733*a*, 733*b* Phase angle for IDC's coated with an ALD-PDMS bilayer 810 location for left supraorbital nerve or cortical stimulation

750 Graph comparing the average pull force under dry conditions and after soaking

761 Average peel force for sample 2.1

762 Average peel force for sample 2.2

763 Average peel force for sample 2.3

764 Average peel force for sample 2.4

765 Average peel force for sample 2.5

810 location for left supraorbital stimulation

820 location for right supraorbital stimulation

830 location for left occipital nerve stimulation

840 location for right occipital nerve stimulation

850 location for deep brain stimulation

860 location for vagus nerve, carotid artery, carotid sinus, phrenic nerve or hypoglossal stimulation

865 location for cerebral spinal cord stimulation

870 location for peripheral nerve stimulation

875 location for spinal cord stimulation

880 location for gastric stimulation

885 location for sacral & pudendal nerve stimulation

890 location for sacral neuromodulation

895 location for fibular nerve stimulation

930 left greater occipital nerve

940 right greater occipital nerve

The invention claimed is:

1. An implantable electrical device comprising:
- a flexible substrate having a first surface and one or more electrical conductors;
- a first biocompatible encapsulation layer;
- a first adhesion layer, disposed between the first surface and the first encapsulation layer; and
- one or more interconnect layers,
- wherein:
  - the first surface comprises a Liquid-Crystal Polymer (LCP);
  - the first adhesion layer is configured and arranged to conform to the first surface;
  - the first encapsulation layer comprises a silicone rubber, and
  - the first adhesion layer and the first encapsulation layer are configured and arranged to resist the ingress of fluids from a human or animal body into at least a portion of the first surface, and
  - the one or more electrical conductors are comprised in the one or more interconnect layers.

2. An implantable electrical device comprising:
- a flexible substrate having a first surface and one or more electrical conductors;
- a first biocompatible encapsulation layer;
- a first adhesion layer, disposed between the first surface and the first encapsulation layer;
- wherein;
  - the first surface comprises a Liquid-Crystal Polymer (LCP);
  - the first adhesion layer is configured and arranged to conform to the first surface;
  - the first encapsulation layer comprises a silicone rubber, and
  - the first adhesion layer and the first encapsulation layer are configured and arranged to resist the ingress of fluids from a human or animal body into at least a portion of the first surface,
- wherein the substrate further comprises a second surface, the electrical device further comprising:
- a second biocompatible encapsulation layer that is physically separate from, and disconnected from, the first biocompatible encapsulation layer; and
- a second adhesion layer, disposed between the second surface and the second encapsulation layer;
- wherein:
  - the second surface comprises a Liquid-Crystal Polymer (LCP);
  - the second adhesion layer is configured and arranged to conform to the second surface;
  - the second encapsulation layer comprises a silicone rubber, and
  - the second adhesion layer and the second encapsulation layer are configured and arranged to resist the ingress of fluids from a human or animal body into at least a portion of the second surface.

3. The implantable electrical device according to claim 1, wherein the silicone rubber comprised in the first encapsulation layer is a polydimethylsiloxane (PDMS) rubber.

4. The implantable electrical device according to claim 1, wherein the first adhesion layer has an average thickness in the range of 50 nm to 100 nm.

5. The implantable electrical device according to claim 1, wherein the first adhesion layer is deposited using an Atomic Layer Deposition (ALD) process.

6. The implantable electrical device according to claim 1, wherein the first surface comprises a substance selected from the group comprising: a polyimide, Parylene-C, SU-8, a polyurethane, or any combination thereof.

7. An implantable electrical device comprising:
- a flexible substrate having a first surface and one or more electrical conductors;
- a first biocompatible encapsulation layer; and
- a first adhesion layer, disposed between the first surface and the first encapsulation layer;
- wherein:
  - the first surface comprises a Liquid-Crystal Polymer (LCP);
  - the first adhesion layer is configured and arranged to conform to the first surface;
  - the first encapsulation layer comprises a silicone rubber,
  - the first adhesion layer and the first encapsulation layer are configured and arranged to resist the ingress of fluids from a human or animal body into at least a portion of the first surface, and the first adhesion layer comprises a ceramic material selected from the group comprising: $HfO_2$, $Al_2O_3$, $Ta_2O_3$, SiC, $Si_3N_4$, $TiO_2$, and any combination thereof.

8. An implantable electrical device comprising:

a flexible substrate having a first surface and one or more electrical conductors;

a first biocompatible encapsulation layer; and a first adhesion layer, disposed between the first surface and the first encapsulation layer;

wherein:

the first surface comprises a Liquid-Crystal Polymer (LCP);

the first adhesion layer is configured and arranged to conform to the first surface;

the first encapsulation layer comprises a silicone rubber, the first adhesion layer and the first encapsulation layer are configured and arranged to resist the ingress of fluids from a human or animal body into at least a portion of the first surface, and the first adhesion layer comprises at least one layer comprising $HfO_2$, adjacent to at least one further layer comprising $Al_2O_3$.

9. An implantable electrical device comprising:

a flexible substrate having a first surface and one or more electrical conductors;

a first biocompatible encapsulation layer; and a first adhesion layer, disposed between the first surface and the first encapsulation layer;

wherein:

the first surface comprises a Liquid-Crystal Polymer (LCP);

the first adhesion layer is configured and arranged to conform to the first surface;

the first encapsulation layer comprises a silicone rubber, the first adhesion layer and the first encapsulation layer are configured and arranged to resist the ingress of fluids from a human or animal body into at least a portion of the first surface, and the first adhesion layer comprises at least one layer comprising $Ta_2O_3$, adjacent to at least one further layer comprising $Al_2O_3$.

10. The implantable electrical device according to claim 1, wherein the first adhesion layer is substantially biocompatible.

11. The implantable electrical device according to claim 1, wherein:

the substrate has a Young's modulus in the range of 2500 to 3600 MPa.

12. The implantable electrical device according to claim 1, wherein the substrate has a maximum thickness of 1 millimeter or less.

13. The implantable electrical device according to claim 1, wherein the first encapsulation layer has a tensile strength in the range of 6 to 8 MPa.

14. The implantable electrical device according to claim 1, wherein the implantable electrical device is comprised in an implantable medical device.

15. The implantable electrical device according to claim 14, wherein the implantable medical device is configured and arranged to provide a degree of sensing, stimulation, data processing, detection or measurement, data storage, oscillation, logic performance, stimulation pulses generation, or any combination thereof.

16. The implantable electrical device according to claim 14, wherein the implantable medical device further comprises:

one or more stimulation electrodes, configured and arranged to transmit energy to human or animal tissue when electrical energy is applied to the one or more electrical conductors.

17. The implantable electrical device according to claim 16, wherein the one or more stimulation electrodes are located along a conformable portion of the substrate.

18. The implantable medical device according to claim 14, configured for stimulating: one or more nerves, one or more muscles, one or more organs, spinal cord tissue, brain tissue, one or more cortical surface regions, one or more sulci, and any combination thereof.

19. The implantable medical device according to claim 14, configured for treatment of: headaches, chronic headaches, primary headaches, incontinence, occipital neuralgia, sleep apnea, hypertension, gastro-esophageal reflux disease, an inflammatory disease, limb pain, leg pain, back pain, lower back pain, phantom pain, chronic pain, epilepsy, an overactive bladder, poststroke pain, obesity, an autoimmune disorder, rheumatoid arthritis, inflammatory bowel disease, Crohn's disease, and any combination thereof.

20. The implantable electrical device according to claim 1, wherein the one or more electrical conductors are completely embedded within the flexible substrate.

21. The implantable electrical device according to claim 1, wherein, in a cross-section of the implantable electrical device, an extent of the first adhesion layer is equal to, or larger than, an extent of the first encapsulation layer.

22. The implantable electrical device according to claim 2, wherein the second adhesion layer comprises a ceramic material.

23. An implantable electrical device comprising:

a flexible substrate having a first surface and one or more electrical conductors;

a first biocompatible encapsulation layer; and a first adhesion layer, disposed between the first surface and the first encapsulation layer;

wherein:

the first surface comprises a Liquid-Crystal Polymer (LCP);

the first adhesion layer is configured and arranged to conform to the first surface;

the first encapsulation layer comprises a silicone rubber, the first adhesion layer and the first encapsulation layer are configured and arranged to resist the ingress of fluids from a human or animal body into at least a portion of the first surface, and in a cross-section of the implantable electrical device, (i) an extent of the first adhesion layer is less than an extent of the first surface, and (ii) an extent of the first encapsulation layer is less than the extent of the first surface.

* * * * *